United States Patent
Yamashita et al.

(10) Patent No.: US 9,592,322 B2
(45) Date of Patent: Mar. 14, 2017

(54) COATING COMPOSITION AND MEDICAL DEVICE

(71) Applicant: TERUMO KABUSHIKI KAISHA, Shibuya-ku (JP)

(72) Inventors: Keiko Yamashita, Ashigarakami-gun (JP); Shigenori Nozawa, Ashigarakami-gun (JP); Masashi Isozaki, Ashigarakami-gun (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 92 days.

(21) Appl. No.: 14/496,504

(22) Filed: Sep. 25, 2014

(65) Prior Publication Data
US 2015/0057746 A1 Feb. 26, 2015

Related U.S. Application Data

(63) Continuation of application No. PCT/JP2013/057494, filed on Mar. 15, 2013.

(60) Provisional application No. 61/721,873, filed on Nov. 2, 2012.

(30) Foreign Application Priority Data

Mar. 27, 2012 (JP) ................................ 2012-071610
Jan. 25, 2013 (JP) ................................ 2013-012181

(51) Int. Cl.
| | | |
|---|---|---|
| *A61L 29/14* | (2006.01) | |
| *A61L 29/08* | (2006.01) | |
| *A61L 29/16* | (2006.01) | |
| *A61L 31/08* | (2006.01) | |
| *A61L 31/10* | (2006.01) | |
| *A61L 31/14* | (2006.01) | |
| *A61L 31/16* | (2006.01) | |
| *A61K 47/36* | (2006.01) | |
| *A61K 31/436* | (2006.01) | |
| *A61K 31/337* | (2006.01) | |
| *A61K 31/728* | (2006.01) | |
| *A61K 9/00* | (2006.01) | |
| *A61K 47/18* | (2006.01) | |
| *A61K 9/70* | (2006.01) | |
| *A61F 2/82* | (2013.01) | |
| *A61M 25/10* | (2013.01) | |

(52) U.S. Cl.
CPC .......... *A61L 29/143* (2013.01); *A61K 9/0024* (2013.01); *A61K 9/7007* (2013.01); *A61K 31/337* (2013.01); *A61K 31/436* (2013.01); *A61K 31/728* (2013.01); *A61K 47/183* (2013.01); *A61K 47/36* (2013.01); *A61L 29/08* (2013.01); *A61L 29/085* (2013.01); *A61L 29/14* (2013.01); *A61L 29/145* (2013.01); *A61L 29/16* (2013.01); *A61L 31/08* (2013.01); *A61L 31/10* (2013.01); *A61L 31/14* (2013.01); *A61L 31/143* (2013.01); *A61L 31/145* (2013.01); *A61L 31/16* (2013.01); *A61F 2/82* (2013.01); *A61L 2300/214* (2013.01); *A61L 2300/416* (2013.01); *A61L 2420/06* (2013.01); *A61M 25/10* (2013.01); *A61M 2025/105* (2013.01)

(58) Field of Classification Search
None
See application file for complete search history.

(56) References Cited

U.S. PATENT DOCUMENTS

| | | | |
|---|---|---|---|
| 5,102,402 A | 4/1992 | Dror et al. | |
| 5,304,121 A | 4/1994 | Sahatjian | |
| 6,268,390 B1 | 7/2001 | Kunz | |
| 6,306,166 B1 * | 10/2001 | Barry | A61L 27/34 623/1.42 |
| 6,364,856 B1 | 4/2002 | Ding et al. | |
| 6,441,025 B2 | 8/2002 | Li et al. | |
| 6,890,339 B2 | 5/2005 | Sahatjian et al. | |
| 7,803,149 B2 | 9/2010 | Bates et al. | |
| 7,811,622 B2 | 10/2010 | Bates et al. | |
| 7,988,987 B2 | 8/2011 | Ranade | |
| 8,100,963 B2 | 1/2012 | Roth et al. | |
| 8,172,793 B2 | 5/2012 | Bates et al. | |

(Continued)

FOREIGN PATENT DOCUMENTS

| | | |
|---|---|---|
| EP | 1 011 743 B1 | 7/2011 |
| JP | 2002-519481 A | 7/2002 |

(Continued)

OTHER PUBLICATIONS

Tomihata, Journal of Biomedical Materials Research, 37, 1997.*
Extended Search Report issued on Jun. 30, 2015 by the European Patent Office, in corresponding European Patent Application No. 137688818.8. (6 pages).
International Search Report (PCT/ISA/210) mailed on May 28, 2013, by the Japanese Patent Office as the International Searching Authority for International Application No. PCT/JP2013/057494.

*Primary Examiner* — Susan Tran
*Assistant Examiner* — William Craigo
(74) *Attorney, Agent, or Firm* — Buchanan, Ingersoll & Rooney PC

(57) ABSTRACT

A coating composition for drug eluting medical devices, which is capable of forming a drug coating layer that is not susceptible to peeling during delivery to a target tissue is provided. This coating composition contains: a water-insoluble drug; at least one selected from the group consisting of hyaluronic acid, alkanoyl hyaluronic acids obtained by substituting at least part of hydrogen atoms in the hydroxyl groups of hyaluronic acid with an alkanoyl group, and salts of hyaluronic acid and the alkanoyl hyaluronic acids; and at least one selected from the group consisting of amino-acid esters and salts thereof. A drug coating layer, a medical device and a method of treatment are also provided.

15 Claims, 3 Drawing Sheets

(56) References Cited

U.S. PATENT DOCUMENTS

| | | |
|---|---|---|
| 8,241,249 B2 | 8/2012 | Wang |
| 8,244,344 B2 | 8/2012 | Wang |
| 8,257,305 B2 | 9/2012 | Speck et al. |
| 8,357,386 B2 | 1/2013 | Hsu |
| 8,366,660 B2 | 2/2013 | Wang |
| 8,366,662 B2 | 2/2013 | Wang |
| 8,403,910 B2 | 3/2013 | Wang |
| 8,404,300 B2 | 3/2013 | Wang |
| 8,414,525 B2 | 4/2013 | Wang |
| 8,414,526 B2 | 4/2013 | Wang |
| 8,414,909 B2 | 4/2013 | Wang |
| 8,414,910 B2 | 4/2013 | Wang |
| 8,425,459 B2 | 4/2013 | Wang |
| 8,439,868 B2 | 5/2013 | Speck et al. |
| 8,512,736 B2 | 8/2013 | Chudzik et al. |
| 2001/0039336 A1* | 11/2001 | Miller ............... A61K 9/0014 536/25.3 |
| 2002/0037358 A1 | 3/2002 | Barry et al. |
| 2004/0234575 A1 | 11/2004 | Horres et al. |
| 2006/0257355 A1 | 11/2006 | Stewart et al. |
| 2006/0286071 A1 | 12/2006 | Epstein et al. |
| 2008/0021385 A1 | 1/2008 | Barry et al. |
| 2008/0031918 A1 | 2/2008 | Lawin et al. |
| 2009/0136560 A1 | 5/2009 | Bates et al. |
| 2010/0015200 A1 | 1/2010 | McClain et al. |
| 2010/0179475 A1 | 7/2010 | Hoffmann et al. |
| 2010/0239635 A1 | 9/2010 | McClain et al. |
| 2010/0286608 A1 | 11/2010 | Tittelbach et al. |
| 2011/0015725 A1 | 1/2011 | Bates et al. |
| 2011/0092900 A1 | 4/2011 | Rubben |
| 2011/0160659 A1 | 6/2011 | Clarke et al. |
| 2011/0160698 A1 | 6/2011 | Hoffmann et al. |
| 2011/0196340 A1 | 8/2011 | Barry et al. |
| 2011/0238011 A1 | 9/2011 | Scheller et al. |
| 2011/0295200 A1 | 12/2011 | Speck et al. |
| 2011/0300221 A1 | 12/2011 | Kunz et al. |
| 2012/0083734 A1 | 4/2012 | Ayres et al. |
| 2012/0239001 A1 | 9/2012 | Barry et al. |
| 2013/0189190 A1 | 7/2013 | Wang |
| 2013/0189329 A1 | 7/2013 | Wang |
| 2013/0197431 A1 | 8/2013 | Wang |
| 2013/0197434 A1 | 8/2013 | Wang |
| 2013/0197435 A1 | 8/2013 | Wang |
| 2013/0197436 A1 | 8/2013 | Wang |
| 2013/0209662 A1 | 8/2013 | Wang et al. |
| 2013/0231638 A1 | 9/2013 | Speck et al. |
| 2014/0005541 A1 | 1/2014 | Bates et al. |
| 2014/0227192 A1 | 8/2014 | Speck et al. |
| 2014/0227193 A1 | 8/2014 | Speck et al. |
| 2014/0227194 A1 | 8/2014 | Speck et al. |
| 2014/0228750 A1 | 8/2014 | Speck et al. |
| 2014/0228751 A1 | 8/2014 | Speck et al. |
| 2014/0228752 A1 | 8/2014 | Speck et al. |

FOREIGN PATENT DOCUMENTS

| | | |
|---|---|---|
| JP | 2004-123785 A | 4/2004 |
| JP | 2005-528149 A | 9/2005 |
| JP | 2006-513791 A | 4/2006 |
| JP | 2010-540159 A | 12/2010 |
| WO | WO 00/01733 A1 | 1/2000 |
| WO | WO 2004/087234 A1 | 10/2004 |
| WO | WO 2009/051614 A1 | 4/2009 |

* cited by examiner

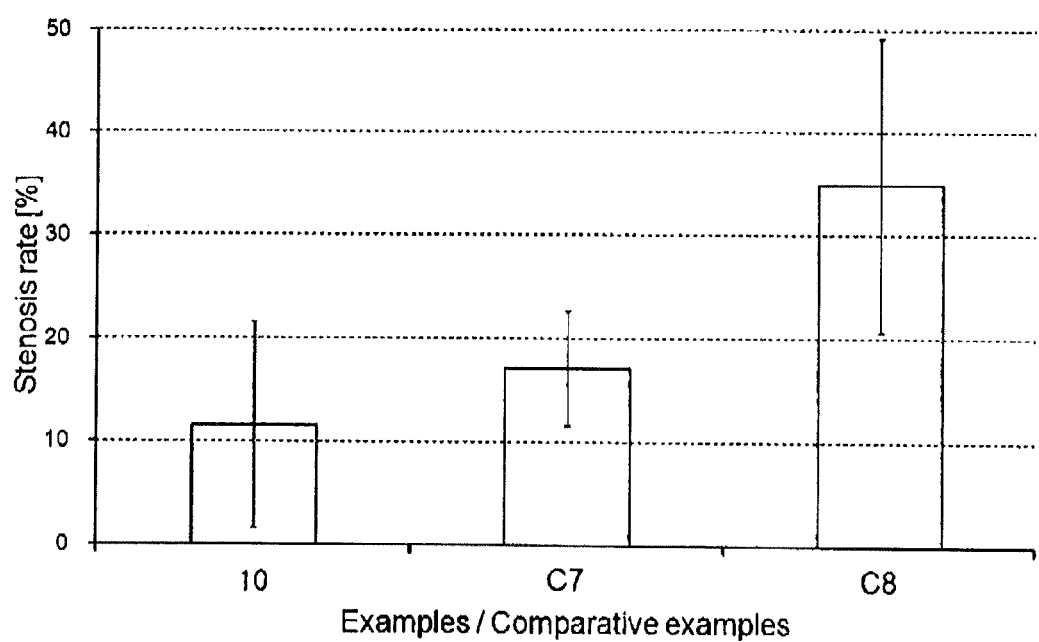

COATING COMPOSITION AND MEDICAL DEVICE

CROSS-REFERENCES TO RELATED APPLICATIONS

This application claims priority as a continuation under 35 U.S.C. §120 to International Application No. PCT/JP2013/057494 filed on Mar. 15, 2013, designating the U.S. and claiming priority to Japanese Application Nos. 2012-071610 filed on Mar. 27, 2012, and 2013-012181 filed on Jan. 25, 2013, and U.S. Provisional Application No. 61/721,873 filed on Nov. 2, 2012, the entire content of all of which are incorporated herein by reference.

TECHNICAL FIELD

Disclosed are a coating composition for a drug-eluting medical device, a drug coating layer of a drug-eluting medical device and/or a drug-eluting medical device coated with the coating composition.

BACKGROUND DISCUSSION

As an example of local drug delivery therapy, there has been a drug-eluting stent (DES).

The DES is so designed as to locally release a drug in a sustained manner for a long period of time, thereby preventing restenosis of a blood vessel. The sustained release of a drug from the DES is achieved by a polymer conjugate such as polylactic acid (PLA). In this case, since the polymer remains in a living body for a long period of time, there is a problem of severe complications such as chronic inflammation or delayed thrombosis at the affected part of a lesion.

Conventionally, it has been reported that sustained release of a drug for a long period of time is necessary for restraining restenosis. In recent years, however, it has been being made clear that by rapid transfer of a drug to a target tissue, even a short-term sustained drug effect is sufficient for successfully preventing restenosis. The technology of rapid drug delivery does not need a polymer matrix, such as PLA or polylactic acid-glycolic acid copolymer (PLGA), for sustained release, and is therefore advantageous for avoiding complications.

In recent years, development of drug-eluting balloons (DEBs) wherein a balloon catheter is coated with a drug has been made positively, and it has been reported to be effective in treating and preventing restenosis. The balloon is coated with a coating that contains a drug and additives, and, when a blood vessel is dilated, the balloon is pressed against the blood vessel wall so as to deliver the drug to the target tissue.

SUMMARY

If the drug is easily peeled from the balloon in the process of delivery of the balloon to the target tissue, however, the amount of the drug remaining on the balloon would be reduced to below a sufficient level for a therapeutic effect, before the balloon is delivered to the affected part of a lesion. In such a situation, the expected therapeutic effect cannot be ensured. In addition, the drug easily peeled off during the delivery process is unnecessarily exposed to the blood, which is undesirable from the viewpoint of safety. Thus, there is a need for a drug coating layer which ensures that a balloon catheter coated with a drug can be delivered to an affected part of the lesion without peeling of the drug, the balloon can be pressed against a blood vessel wall simultaneously with expansion, and the drug can thereby be released rapidly.

It has been reported that a hydrophilic drug can be delivered by use of a balloon catheter coated with a hydrogel of a hydrophilic polymer. On the other hand, in the case of a water-insoluble drug, it may be difficult for the drug to be mixed with a hydrophilic polymer so as to form a hydrogel. In such a case, it is difficult to effectively deliver the drug. Even if the intended mixing can be achieved, the coating layer in which the highly hydrophilic polymer and the drug are mixed with each other is poor in adhesion to medical devices, and it is considered that due to the influence of the high polarity of the polymer, the drug would be easily eluted into the blood during the delivery to a target tissue. In the case where a hydrophilic polymer is used, therefore, the coating layer would be easily separated during the process of delivery to the affected part of the lesion, so that it is difficult to enhance the transferability of the drug to the target tissue.

On the other hand, in the case where use is made of such a hydrophobic polymer having high hydrophobicity as to be insoluble in water, the hydrophobic interaction of the hydrophobic polymer with the water-insoluble drug is so strong that there arises the following problem. Although the durability of the drug coating layer during the delivery process is improved, the strong hydrophobic interaction between the drug and the hydrophobic polymer makes it impossible for the drug to be rapidly released at the affected part of the lesion. In addition, the hydrophobic interaction between molecules of the water-insoluble hydrophobic drug is strengthened, so that the drug would aggregate with each other and on the surface of the medical device, making it impossible to achieve a uniform coating. The aggregated state of the drug in the coating in such a case leads to easy separation of the drug during handling of the medical device, which is undesirable from the viewpoints of safety and function.

Besides, if a low-molecular compound provided in the coating together with the drug is excessively high in hydrophobicity, the hydrophobic interaction between the low-molecular compound and the water-insoluble drug would be strong, and hydrophobic regions of them have a high affinity for the balloon surface. As a result, release (transfer) of the drug from the balloon to the affected part (the inner surface of the blood vessel) would not easily occur, even upon contact of the balloon with the affected part. Furthermore, if the hydrophobicity of the low-molecular compound mixed with the hydrophobic drug is strong, the hydrophobic interaction between molecules of the water-insoluble drug would be so strong that the drug may easily aggregate on the surface of the medical device, making it difficult to achieve a uniform coating. In addition, the drug applied to the medical device surface in an aggregated state can easily come off the balloon surface during handling of the medical device, which is undesirable from the viewpoints of safety and function.

If the low-molecular compound is excessively hydrophilic, on the other hand, it may be difficult for the compound to be mixed with the water-insoluble drug. In such a case, it may be difficult to prepare a stable drug coating layer solution, or the low-molecular compound may be easily dissolved by the bloodstream together with the drug, due to the strong hydrophilicity thereof. Therefore, the low-molecular compound used in the coating together with the drug is desired to have both a hydrophilic region, for relaxing the hydrophobic interaction between the molecules of the water-insoluble drug and ensuring uniform dispersion of the drug, and a hydrophobic region that has an affinity for the water-insoluble drug.

Accordingly, for the compounds mixed with the water-insoluble drug, both in the case of the polymer and in the case of the low-molecular compound, the balance of polarity for good miscibility with the water-insoluble drug is important.

Thus, there is a need for a drug coating layer of a medical device which ensures that a drug can be delivered for treatment of an affected blood vessel part such as restenosis, without easy peeling of the drug from the medical device in the process of delivery to a target tissue, that the drug can be rapidly released at the affected part of the lesion after the delivery, and that transferability of the drug to the target tissue can be enhanced.

According to an illustrative aspect, disclosed is a coating composition for drug-eluting medical devices which makes it possible to form a drug coating layer that is not easily peeled in the process of delivery to a target tissue, and also makes it possible for the drug to be rapidly released at the affected part.

It has been determined that when a coating composition containing: a water-insoluble drug which is at least one selected from the group consisting of hyaluronic acid, alkanoyl hyaluronic acids obtained by substituting at least part of hydrogen atoms in hydroxyl groups of hyaluronic acid with an alkanoyl group, and salts of hyaluronic acid and the alkanoyl hyaluronic acids; and at least one selected from the group consisting of amino-acid esters and salts thereof, is used, it is possible to form a drug coating layer on a surface of a medical device, the drug coating layer ensuring that the drug is not easily be peeled in the process of delivery to a target tissue and that the drug can be rapidly released (transferred) to an inner surface of a blood vessel, simultaneously with expansion of the medical device at the target tissue.

Disclosed are the following aspects (1) to (16).

(1) A coating composition for a drug-eluting medical device, the coating composition containing:
a water-insoluble drug;
at least one selected from the group consisting of hyaluronic acid, alkanoyl hyaluronic acids obtained by substituting at least part of hydrogen atoms in hydroxyl groups of hyaluronic acid with an alkanoyl group, and salts of hyaluronic acid and the alkanoyl hyaluronic acids; and
at least one selected from the group constituting of amino-acid esters and salts thereof.

(2) The coating composition according to the above paragraph (1),
wherein the alkanoyl group is represented by the following formula:

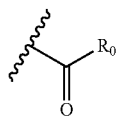

where $R_0$ is selected from the group consisting of alkyl groups of up to five carbon atoms, benzyl group and phenyl group.

(3) The coating composition according to the above paragraph (1) or (2), wherein the alkanoyl group is at least one selected from the group consisting of acetyl group, propionyl group, isobutyryl group and butyryl group.

(4) The coating composition according to any of the above paragraphs (1) to (3),
wherein the number of the hydrogen atoms in the hydroxyl groups that are substituted with the alkanoyl group is, on an average, 0.01 to 4 per unit of the hyaluronic acid.

(5) The coating composition according to any of the above paragraphs (1) to (4),
wherein the average molecular weight of the at least one selected from the group consisting of hyaluronic acid, alkanoyl hyaluronic acids obtained by substituting at least part of the hydrogen atoms in the hydroxyl groups of the hyaluronic acid with an alkanoyl group, and salts of hyaluronic acid and the alkanoyl hyaluronic acids is $5 \times 10^3$ to $2 \times 10^5$.

(6) The coating composition according to any of the above paragraphs (1) to (5),
wherein the amino-acid ester is represented by the following formula:

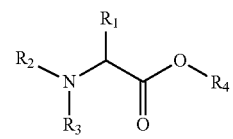

where $R_1$ is a hydrogen atom, methyl group, guanidinopropyl group, carbamoylmethyl group, carboxymethyl group, methoxycarbonylmethyl group, ethoxycarbonylmethyl group, mercaptomethyl group, 2-carbamoylethyl group, 2-carboxyethyl group, 2-methoxycarbonylethyl group, 2-ethoxycarbonylethyl group, (1H-imidazol-4-yl)methyl group, 1-methylpropyl group, 2-methylpropyl group, 4-aminobutyl group, 2-(methylthio)ethyl group, benzyl group, hydroxymethyl group, 1-hydroxyethyl group, (1H-indol-3-yl)methyl group, 4-hydroxybenzyl group or isopropyl group or forms a trimethylene group together with $R_2$; $R_2$ is hydrogen atom or forms trimethylene group together with $R_1$; $R_3$ is a hydrogen atom, an alkyl group of up to five carbon atoms, benzyl group or benzoyl group; and $R_4$ is an alkyl group of up to five carbon atoms, benzyl group or phenyl group.

(7) The coating composition according to any of the above paragraphs (1) to (6),
wherein the amino-acid ester is a methyl ester or ethyl ester of an amino acid selected from the group consisting of L-alanine, L-arginine, L-asparagine, L-cysteine, L-glutamine, glycine, L-histidine, L-isoleucine, L-leucine, L-lycine, L-methionine, L-phenylalanine, L-proline, L-serine, L-threonine, L-tryptophan, L-valine, N-benzylglycine, and N-α-benzoyl-L-arginine or a monomethyl ester, dimethyl ester, monoethyl ester or diethyl ester of any one amino acid selected from the group consisting of L-aspartic Acid and L-glutamic acid.

(8) The coating composition according to any of the above paragraphs (1) to (7),
wherein the mass ratio (A/B) of the content (A) of hyaluronic acid, the alkanoyl hyaluronic acid obtained by substituting at least part of the hydrogen atoms in the hydroxyl groups of hyaluronic acid with an alkanoyl group or the salt of hyaluronic acid or the alkanoyl hyaluronic acid to the content (B) of the amino-acid ester or the salt thereof is in the range from 0.0008 to 0.8 (mass/mass).

(9) The coating composition according to any of the above paragraphs (1) to (8), further containing a lower alcohol.

(10) The coating composition according to the above paragraph (9), wherein the lower alcohol is glycerine.

(11) The coating composition according to any of the above paragraphs (1) to (10), wherein the water-insoluble drug is at least one selected from the group consisting of paclitaxel, rapamycin, docetaxel and everolimus.

(12) The coating composition according to any of the above paragraphs (1) to (11), wherein the medical device is a medical device that is radially expandable within a lumen.

(13) The coating composition according to the above paragraph (12), wherein the medical device that is radially expandable within the lumen is a balloon catheter or a stent.

(14) A drug coating layer formed on at least part of a surface of a medical device by use of the coating composition according to any of the above paragraphs (1) to (13).

(15) A medical device which is radially expandable within a lumen and which is coated with the coating composition according to any of the above paragraphs (1) to (11).

(16) A method of treatment, including:
a step of delivering the medical device according to the above paragraph (15) into a lumen;
a step of radially expanding the medical device within the lumen; and
a step of eluting a drug from a drug coating layer formed on at least part of a surface of the medical device and allowing the drug to act on the lumen.

According to the disclosed aspects, it is possible to provide a coating composition for drug-eluting medical devices which makes it possible to form a drug coating layer that would not be easily peeled during the process of delivery to a target tissue and also that would rapidly release (transfer) the drug to an inner surface of a blood vessel, simultaneously with expansion of the medical device at the target tissue.

When a drug-eluting medical device having a drug coating layer formed by use of the coating composition according to the described aspects is used, the drug can be efficiently delivered to an affected part of lesion, while restraining separation of the drug coating layer. Moreover, within an expansion time of one to two minutes at the affected part of lesion, the drug can be rapidly released, and transferability of the drug to the tissue can be enhanced.

BRIEF DESCRIPTION OF THE DRAWINGS

In FIG. 1, reference numeral 1 is an imitative blood vessel, reference numeral 2 is a guiding catheter, reference numeral 3 is a balloon catheter, and reference numeral 4 is a balloon.

FIG. 5 is a graph representing stenosis rate in Example 10 and Comparative Examples C7 and C8, in evaluation of the effectiveness in a swine coronary artery.

DETAILED DESCRIPTION

1. Coating Composition

Figure 1:
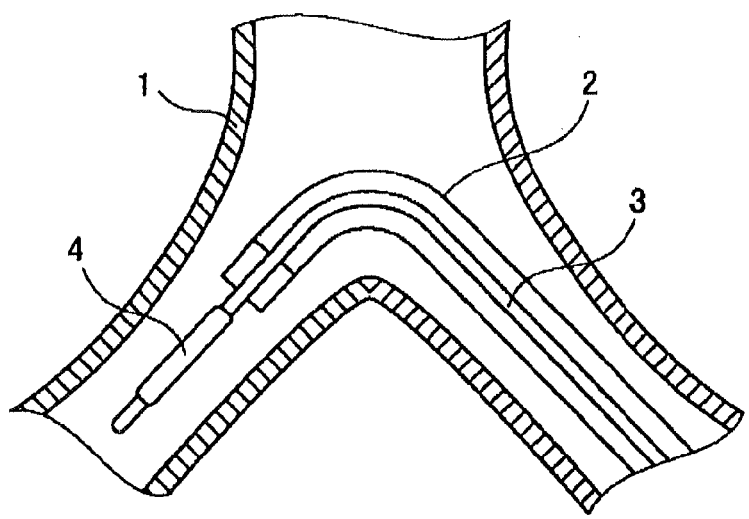
FIG. 1 is a schematic sectional view of an experimental apparatus used in a drug coating layer durability evaluation test using an imitative blood vessel, in a state in which a balloon catheter is inserted in a guiding catheter disposed in the imitative blood vessel.

The coating composition is a coating composition for drug-eluting medical devices, which contains: a water-insoluble drug; at least one selected from the group consisting of hyaluronic acid, alkanoyl hyaluronic acids obtained by substituting at least part of hydrogen atoms in hydroxyl groups of hyaluronic acid with an alkanoyl group, and salts of hyaluronic acid and the alkanoyl hyaluronic acids; and at least one selected from the group consisting of amino-acid esters and salts thereof.

The coating composition is a blend in which the water-insoluble drug, the at least one selected from the group consisting of hyaluronic acid, alkanoyl hyaluronic acids obtained by substituting at least part of the hydrogen atoms in the hydroxyl groups of hyaluronic acid with an alkanoyl group and salts of hyaluronic acid and the alkanoyl hyaluronic acids, and the at least one selected from the group consisting of amino-acid esters and salts thereof are blended with each other. These ingredients are not bonded to each other by a covalent bond.

The amino-acid esters and salts thereof that are blended in the coating composition can be enhanced in polarity (water-solubility) by salts of amino groups, for example, hydrochlorides of amino groups, and can exhibit different properties such as hydrophilic property or hydrophobic property and basic property or acidic property, depending on side chains of the amino acids. The amino-acid ester compounds and salts thereof coexist with hyaluronic acid, alkanoyl hyaluronic acids obtained by substituting at least part of the hydrogen atoms in the hydroxyl groups of hyaluronic acid with an alkanoyl group and salts of hyaluronic acid and the alkanoyl hyaluronic acids, which have hydrophilic regions, and, therefore, side chains of the amino-acid ester compounds and salts thereof may be either polar or non-polar. Preferably, the side chains of the amino-acid ester compounds and salts thereof are non-polar, since hyaluronic acid, the alkanoyl hyaluronic acids and salts thereof are polar.

(1) Water-Insoluble Drug

The water-insoluble drug means a drug which is insoluble or difficulty soluble in water, specifically a drug which has a solubility in water of less than 5 mg/mL at pH 5 to 8. The solubility may be less than 1 mg/mL, or may further be less than 0.1 mg/mL. The water-insoluble drug includes fat-soluble drugs.

Preferable examples of the water-insoluble drug include immunosuppressants, e.g., cyclosporins inclusive of cyclosporin, immunoadjuvants such as rapamycin, etc., carcinostatics such as paclitaxel, etc., antiviral or antibacterial agents, antineoplastic agents, analgesic and anti-inflammatory agents, antibiotics, antiepileptics, anxiolytic agents, antiparalytic agents, antagonists, neuron blocking agents, anticholinergic and cholinergic agents, muscarine antagonists and muscarine agents, antiadrenergic agents, antiarrhythmic agents, antihypertensive agents, hormone preparations and nutritional supplements.

The water-insoluble drug is preferably at least one selected from the group consisting of rapamycin, paclitaxel, docetaxel and everolimus. The rapamycin, paclitaxel, docetaxel, and everolimus include their analogs and/or derivatives, provided that the analogs and/or derivatives have a drug effect equivalent to the original. For instance, paclitaxel and docetaxel are in an analogous relationship, whereas rapamycin and everolimus are in a derivative relationship. Among these, more preferred is paclitaxel.

(2) At least one selected from the group consisting of hyaluronic acid, alkanoyl hyaluronic acids obtained by substituting at least part of hydrogen atoms in hydroxyl groups of hyaluronic acid with an alkanoyl group, and salts of hyaluronic acid and the alkanoyl hyaluronic acids (2.1) Hyaluronic Acid and Salts Thereof As represented by the following formula, hyaluronic acid has repeating units in which two sugars, namely, glucuronic acid and N-acetylglucosamine are alternately linked on a straight chain (n is a positive integer), and the linkages are β-1,3-glycoside linkage and β-1,4-glycoside linkage.

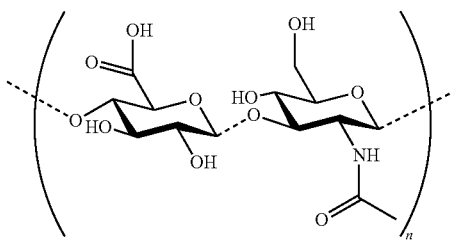

The salt of hyaluronic acid is not specifically restricted. The salt is preferably an alkali metal salt, more preferably sodium salt.

The average molecular weight of hyaluronic acid or salt thereof is not particularly limited. Preferably, hyaluronic acid or salt thereof has an average molecular weight of $5 \times 10^3$ to $2 \times 10^5$, more preferably $8 \times 10^4$ to $1.2 \times 10^5$, and further preferably $1 \times 10^5$.

(2.2) Alkanoyl Hyaluronic Acids and Salts Thereof

The alkanoyl hyaluronic acid is a hyaluronic acid derivative obtained by substituting at least part of hydrogen atoms in hydroxyl groups of hyaluronic acid with an alkanoyl group, and one unit thereof is represented by the following formula:

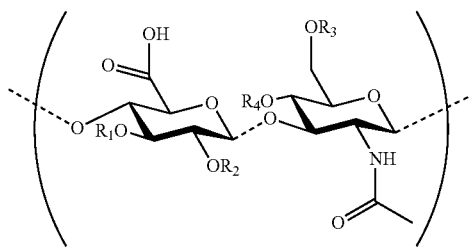

where $R_1$, $R_2$, $R_3$ and $R_4$ are each independently a hydrogen atom or an alkanoyl group.

The alkanoyl group is not specifically restricted. The alkanoyl group is preferably one that is represented by the following formula:

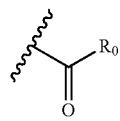

where $R_0$ is selected from the group consisting of alkyl groups of up to five carbon atoms, benzyl group and phenyl group, more preferably acetyl group ethanoyl group), propionyl group (propanoyl group), isobutyryl group (2-methylpropanoyl group) or butyryl group (butanoyl group), and further preferably acetyl group (ethanoyl group).

The number of the hydrogen atoms in the hydroxyl groups of hyaluronic acid that are substituted with an alkanoyl group is not particularly limited. The number, on average, is preferably 0.01 to 4/unit, more preferably 2.0 to 4.0/unit, and further preferably 2.5 to 4.0/unit.

The salt of the alkanoyl hyaluronic acid is not specifically restricted. The salt is preferably an alkali metal salt, more preferably a sodium salt.

The average molecular weight of the alkanoyl hyaluronic acid or salt thereof is not particularly limited. The alkanoyl hyaluronic acid or salt thereof preferably has an average molecular weight of $5 \times 10^3$ to $2 \times 10^5$, more preferably $8 \times 10^4$ to $1.2 \times 10^5$, and further preferably $1 \times 10^5$.

Of hyaluronic acid and the alkanoyl hyaluronic acid, preferred is the alkanoyl hyaluronic acid. The alkanoyl hyaluronic acid has a hydrophobic moiety and a hydrophilic moiety. The hydrophobic moiety can enhance affinity for the water-insoluble drug and the surfaces of medical devices, whereas the hydrophilic moiety prevents the molecules of the water-insoluble drug from aggregating under hydrophobic interaction. Therefore, when the coating composition contains the alkanoyl hyaluronic acid, the water-insoluble drug can be allowed to coat a surface of a medical device more uniformly and stably.

In addition, hyaluronic acid and derivatives thereof are highly biocompatible (for example, they do not induce thrombus formation) and are biodegraded rapidly, so that they are preferable from the viewpoint of safety.

The coating composition contains hyaluronic acid, the alkanoyl hyaluronic acid obtained by substituting at least part of the hydrogen atoms in the hydroxyl group of hyaluronic acid with an alkanoyl group and/or the salts of the hyaluronic acid and the alkanoyl hyaluronic acid, in a total amount of preferably 0.1 to 10 parts by mass, more preferably 1.0 to 5.0 parts by mass, and further preferably 2.0 to 5.0 parts by mass, based on 100 parts by mass of the water-insoluble drug.

(3) At least one selected from the group consisting of amino-acid esters and salts thereof (3.1) Amino-Acid Esters The amino-acid ester is not specifically restricted insofar as it is an ester of an amino acid with an alcohol or a phenol. Preferably, however, the amino-acid ester is an ester of an amino acid with an alcohol. More preferably, the amino-acid ester is one that is represented by the following formula:

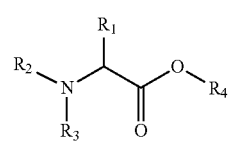

where $R_1$ is a hydrogen atom, methyl group, guanidinopropyl group, carbamoylmethyl group, carboxymethyl group, methoxycarbonylmethyl group, ethoxycarbonylmethyl group, mercaptomethyl group, 2-carbamoylethyl group, 2-carboxyethyl group, 2-methoxycarbonylethyl group, 2-ethoxycarbonylethyl group, (1H-imidazol-4-yl)methyl group, 1-methylpropyl group, 2-methylpropyl group, 4-aminobutyl group, 2-(methylthio)ethyl group, benzyl group, hydroxymethyl group, 1-hydroxyethyl group, (1H-indol-3-yl)methyl group, 4-hydroxybenzyl group or isopropyl group or forms a trimethylene group together with $R_2$; $R_2$ is hydrogen atom or forms a trimethylene group together with $R_1$; $R_3$ is a hydrogen atom, an alkyl group of up to five carbon atoms, benzyl group or benzoyl group; and $R_4$ is an alkyl group of up to five carbon atoms, benzyl group or phenyl group.

Further preferably, the amino-acid ester is a methyl ester or ethyl ester of an amino acid selected from the group consisting of L-alanine, L-arginine, L-asparagine, L-cysteine, L-glutamine, glycine, L-histidine, L-isoleucine, L-leucine, L-lycine, L-methionine, L-phenylalanine, L-proline, L-serine, L-threonine, L-tryptophan, L-valine, N-benzylglycine, and N-α-benzoylarginine or a monomethyl ester, dimethyl ester, monoethyl ester or diethyl ester of an amino acid selected from the group consisting of L-aspartic acid and L-glutamic acid. Still more preferably, the amino-acid ester is L-valine methyl ester, L-phenylalanine methyl ester, L-alanine ethyl ester, N-benzylglycine ethyl ester, L-arginine ethyl ester, N-α-benzoyl-L-arginine ethyl ester, dimethyl L-aspartate or L-serine ethyl ester. Still further preferably, the amino-acid ester is L-valine methyl ester or dimethyl L-aspartate.

(3.2) Salts of Amino-Acid Esters

The salt of an amino-acid ester is preferably a salt of the aforementioned amino-acid ester with an inorganic or organic acid such as hydrochloric acid, acetic acid, etc., more preferably a hydrochloride of the aforementioned amino-acid ester. Where there is a free carboxyl group which is not part of an ester linkage, salts of the aforementioned amino-acid esters with alkali metals such as sodium are also preferable.

The coating composition contains at least one selected from the group consisting of hyaluronic acid, alkanoyl hyaluronic acids obtained by substituting at least part of hydrogen atoms in hydroxyl groups of hyaluronic acid with an alkanoyl group and salts of hyaluronic acid and the alkanoyl hyaluronic acids, and at least one selected from the group consisting of amino-acid esters and salts thereof, whereby it is made possible to more effectively prevent the separation of the drug coating layer during the delivery process.

(4) Content Ratio

In the coating composition, the mass ratio (A/B) of the content (A) of the at least one selected from the group consisting of hyaluronic acid, the alkanoyl hyaluronic acids obtained by substituting at least part of the hydrogen atoms in the hydroxyl groups of hyaluronic acid with an alkanoyl group and salts of hyaluronic acid and the alkanoyl hyaluronic acids to the content (B) of the at least one selected from the group consisting of the amino-acid esters and salts thereof is preferably in the range from 0.0008 to 0.8 (mass/mass), more preferably from 0.008 to 0.4 (mass/mass), and further preferably from 0.016 to 0.16 (mass/mass).

(5) Combination

The combination of the water-insoluble drug, the at least one selected from the group consisting of hyaluronic acid, the alkanoyl hyaluronic acids obtained by substituting at least part of the hydrogen atoms in the hydroxyl groups of hyaluronic acid with an alkanoyl group and salts of hyaluronic acid and the alkanoyl hyaluronic acids, and the at least one selected from the group consisting of amino-acid esters and salts thereof, is not specifically restricted. As a preferable combination, there may be mentioned a combination of acetylhyaluronic acid with L-valine methyl ester and/or dimethyl L-aspartate. As another preferable combination, there may be mentioned a combination of acetylhyaluronic acid with L-phenylalanine ethyl ester/L-serine ethyl ester.

(6) Other Preferable Ingredients

Preferably, the coating composition further contains a lower alcohol. When the coating composition contains a lower alcohol, the water-insoluble drug's property for penetration into blood vessels can be enhanced, and uniformity of the drug coating layer can be enhanced. The lower alcohol is not specifically restricted, insofar as it is an alcohol of up to five carbon atoms. Preferably, the lower alcohol is a triol or tetraol of up to five carbon atoms. More preferably, the lower alcohol is glycerine (also referred to as "glycerol" or "propane-1,2,3-triol"), 1,2,4-butanetriol (also referred to as "butane-1,2,4-triol") or erythritol (also referred to as "(2R, 3S)-butane-1,2,3,4-tetraol"). Further preferably, the lower alcohol is glycerine.

In the case where the composition contains the lower alcohol, its content is not particularly limited. The lower alcohol content is preferably 10 to 500 parts by weight, more preferably 30 to 300 parts by weight, and further preferably 50 to 200 parts by weight, based on 100 parts by weight of the water-insoluble drug.

(7) Other Ingredients which May be Contained

In addition to the aforementioned ingredients, the coating composition may contain a solvent for the ingredients, such as water, ethanol, acetone, tetrahydrofuran, etc. Furthermore, the coating composition may contain other additives on condition that the additives are not detrimental to the effect of the coating composition.

2. Drug Coating Layer

The drug coating layer is a layer formed from the coating composition. The drug coating layer is a layer which contains the water-insoluble drug, the at least one selected from the group consisting of hyaluronic acid, alkanoyl hyaluronic acids obtained by substituting at least part of hydrogen atoms in hydroxyl groups of hyaluronic acid with an alkanoyl group and salts of hyaluronic acid and the alkanoyl hyaluronic acids, and the at least one selected from the group consisting of amino-acid esters and salts thereof. The drug coating layer has a high affinity for the surface of a medical device, so that it would not easily be peeled or separated during the delivery process of the medical device, and, yet, it can swiftly release the drug at a target tissue.

The drug coating layer can be formed by coating a surface of a medical device with the coating composition, followed by drying. This method, however, is not restrictive.

The amount of the drug contained in the drug coating layer is not particularly limited. The drug is preferably contained in the drug coating layer in a density of 0.1 to 10 µg/mm$^2$, more preferably 0.5 to 5 µg/mm$^2$, further preferably 0.5 to 3.5 µg/mm$^2$, and still further preferably 1.0 to 3.0 µg/mm$^2$.

3. Drug-Eluting Medical Device

The drug-eluting medical device has the drug coating layer, either directly on a surface thereof or on a surface thereof having been pretreated with an organic solvent, primer irradiation, irradiation with UV rays, or the like. The medical device is preferably a medical device which is radially (circumferentially) expandable in a lumen such as a blood vessel, more preferably a balloon catheter or a stent.

On at least part of a surface of the drug-eluting medical device is formed the drug coating layer that contains the water-insoluble drug, the at least one selected from the group consisting of hyaluronic acid, alkanoyl hyaluronic acids obtained by substituting at least part of hydrogen atoms in hydroxyl groups of hyaluronic acid with an alkanoyl group and salts of hyaluronic acid and the alkanoyl hyaluronic acids, and the at least one selected from the group consisting of amino-acid esters and salts thereof. The drug coating layer has a high affinity for the surface of the medical device, so that it is not susceptible to peeling or separation during the process of delivery of the medical device. Furthermore, the drug coating layer has a high affinity for the tissue of an affected part of lesion, so that the drug is expected to be rapidly eluted at the target tissue. In the case of a balloon catheter, the drug coating layer is formed on an outer surface of an expandable portion (balloon). In the case of a stent, the drug coating layer is formed on an outer surface of an expandable portion.

The material of the expandable portion of the medical device is preferably a material which has a certain degree of flexibility and has a certain degree of rigidity such that upon arrival at a blood vessel, tissue or the like the expandable portion is expanded so that the drug can be released from the drug coating layer present on the surface of the expandable portion. Specifically, the surface of the expandable portion on which the drug coating layer is provided is formed of a resin. The resin constituting the surface of the expandable portion is not specifically restricted, and preferable examples of the material include polyamides. In other words, at least part of the surface of the expandable portion of the medical device to be coated with the drug is made of a polyamide. The polyamide is not specifically restricted insofar as it is a polymer having an amide linkage. Examples of the polyamide include aromatic polyamides, for example, homopolymers such as polytetramethylene adipamide (nylon 46), polycaprolactam (nylon 6), polyhexamethylene adipamide (nylon 66), polyhexamethylene sebacamide (nylon 610), polyhexamethylene dodecamide (nylon 612), polyundecanolactam (nylon 11), polydodecanolactam (nylon 12), etc., copolymers such as caprolactam/lauryllactam copolymer (nylon 6/12), caprolactam/aminoundecanoic acid copolymer (nylon 6/11), caprolactam/ω-aminononanoic acid copolymer (nylon 6/9), caprolactam/hexamethylenediammonium adipate copolymer (nylon 6/66), etc., copolymer of adipic acid with metaxylenediamine, and copolymers of hexamethylenediamine with m,p-phthalic acids, etc. Furthermore, polyamide elastomers which are block copolymers having nylon 6, nylon 66, nylon 11, nylon 12 or the like as a hard segment and having a polyalkylene glycol, a polyether, an aliphatic polyester or the like as a soft segment can also be used as a base material for the medical device. The polyamides may be used either singly or in combination of two or more of them.

In addition, for other portions than the expandable portion of the medical device, there can be used thermoplastic resins, for example, polyolefins such as polyethylene, polypropylene, ethylene-propylene copolymer, etc., polyesters such as polyethylene terephthalate, etc., polyvinyl chloride, ethylene-vinyl acetate copolymer, crosslinked ethylene-vinyl acetate copolymer, polyurethane, etc., polyamides, polyamide elastomers, silicone rubbers, latex rubbers, and so on.

4. Method of Treatment in which Drug-Eluting Medical Device is Used

A method of treatment in which the drug-eluting medical device is used includes a step of eluting the drug from the drug coating layer formed on at least part of the surface of the medical device. To be more specific, the method of treatment in which the drug-eluting medical device is used preferably includes: a step of delivering the medical device into a lumen; a step of radially expanding the medical device inside the lumen; and a step of eluting the drug from the drug coating layer formed on at least part of the surface of the medical device, thereby allowing the drug to act on the lumen.

The step of delivering the drug-eluting medical device into the lumen can be carried out in the same manner as in the cases of conventionally known balloons and stents. For instance, in the case where the drug-eluting balloon or stent is to be delivered to a stenosed part of a coronary artery, a tube-shaped guiding catheter is inserted via a patient's carpal or femoral artery to an inlet portion of a cardiac coronary artery, a guide wire is inserted into the guiding catheter, and the balloon catheter is inserted along the guide wire, whereby the balloon or stent can be delivered to the stenosed part.

The step of radially expanding the drug-eluting medical device in the lumen can be carried out in the same manner as in the cases of conventionally known balloons and stents.

The step of eluting the drug from the drug coating layer formed on at least part of the surface of the drug-eluting medical device to permit the drug to act on the lumen can be carried out by a method in which the medical device expanded inside the lumen is held for a time of several tens of seconds to several minutes while keeping the drug-eluting balloon expanded or in which the drug-eluting stent is placed indwelling in the lumen. This ensures that the lumen is expanded and the drug of the drug coating layer acts on the tissue of the lumen.

The method of treatment in which the drug-eluting medical device is used can be applied, for example, to treatment of angiostenosis. According to the method of treatment, it is possible to prevent restenosis, by utilizing a cell proliferation-suppressing agent such as carcinostatic (e.g., paclitaxel) or immunosuppressant as the drug.

The hyaluronic acid or the alkanoyl hyaluronic acid or salt thereof contained in the coating composition is highly biocompatible (for example, it would not induce thrombus formation) and is rapidly biodegraded. Accordingly, it is possible to provide a drug-eluting medical device that is preferable from the viewpoint of safety.

EXAMPLES

Now, various illustrative embodiments will be described more in detail below, by showing examples. It is to be noted, however, that the above-described aspects are not restricted to the following examples.

Fabrication or preparation of drug-eluting balloon, or preparation of non-drug-coated balloon Example 1

(1) Preparation of Coating Solution 1

1-1) Sodium acetylhyaluronate (average molecular weight=100,000; degree of substitution with acetyl group=2.6 to 3.8/unit; CAS No. 287390-12-9) in an amount of 5 mg was weighed, and was added to and dissolved in an anhydrous ethanol-water mixture containing 0.8 mL of anhydrous ethanol and 0.2 mL of reverse osmosis (RO) water, to prepare a 0.5% acetylhyaluronic acid solution.

1-2) L-Valine methyl ester hydrochloride (CAS No. 6306-52-1) in an amount of 54 mg was weighed, and was added to and dissolved in an anhydrous ethanol-water mixed solution containing 1.5 mL of anhydrous ethanol and 0.3 mL of RO water, to prepare a 30 mg/mL valine methyl ester solution.

1-3) Paclitaxel (CAS No. 33069-62-4) in an amount of 80 mg was weighed, and was added to and dissolved in an anhydrous ethanol-acetone mixed solution containing 1 mL of anhydrous ethanol and 1 mL of acetone, to prepare a 40 mg/mL paclitaxel solution.

1-4) A coating solution 1 was prepared by mixing 30 μL of the 0.5% acetylhyaluronic acid solution, 120 μL of the 30 mg/mL valine methyl ester solution, and 150 μL of the 40 mg/mL paclitaxel solution.

(2) Coating of Balloon with Drug

A balloon catheter (produced by Terumo Corporation, the material of a balloon (expandable portion) is nylon elastomer), whose expandable portion is sized to be 3.0 mm in diameter and 20 mm in length when expanded, was prepared. The balloon in its expanded state was coated with the coating solution 1 so that the amount of paclitaxel would be about 3 μg/mm$^2$, by use of a pipette, followed by drying the balloon, to fabricate a drug-eluting balloon.

Example 2

(1) Preparation of Coating Solution 2

1-1) L-Phenylalanine ethyl ester hydrochloride (CAS No. 3182-93-2) in an amount of 54 mg was weighed, and was added to and dissolved in an anhydrous ethanol-water mixed solution containing 1.5 mL of anhydrous ethanol and 0.3 mL of RO water, to prepare a 30 mg/mL phenylalanine ethyl ester solution.

1-2) A 0.5% acetylhyaluronic acid solution was prepared in the same manner as in Example 1.

1-3) A 40 mg/mL paclitaxel solution was prepared in the same manner as in Example 1.

1-4) A coating solution 2 was prepared by mixing 120 μL of the 30 mg/mL phenylalanine ethyl ester solution, 30 μL of the 0.5% acetylhyaluronic acid solution, and 150 μL of the 40 mg/mL paclitaxel solution.

(2) Coating of Balloon with Drug

A drug-eluting balloon was fabricated in the same manner as in Example 1, while using the coating solution 2 prepared above in such a manner that the amount of paclitaxel would be about 2 μg/mm$^2$.

Example 3

(1) Preparation of Coating Solution 3

1-1) L-Alanine ethyl ester hydrochloride (CAS No. 1115-59-9) in an amount of 80 mg was weighed, and was added to and dissolved in an anhydrous ethanol-water mixed solution containing 1 mL of anhydrous ethanol and 1 mL of RO water, to prepare a 40 mg/mL alanine ethyl ester solution.

1-2) A 0.5% acetylhyaluronic acid solution was prepared in the same manner as in Example 1.

1-3) A 40 mg/mL paclitaxel solution was prepared in the same manner as in Example 1.

1-4) A coating solution 3 was prepared by mixing 120 μL of the 40 mg/mL alanine ethyl ester solution, 30 μL of the 0.5% acetylhyaluronic acid solution, and 150 μL of the 40 mg/mL paclitaxel solution.

(2) Coating of Balloon with Drug

A drug-eluting balloon was fabricated in the same manner as in Example 1, while using the coating solution 3 prepared above in such a manner that the amount of paclitaxel would be about 2 μg/mm$^2$.

Example 4

(1) Preparation of Coating Solution 4

1-1) N-Benzylglycine ethyl ester (CAS No. 6436-90-4) in an amount of 80 mg was weighed, and was added to and dissolved in an anhydrous ethanol-water mixed solution containing 1 mL of anhydrous ethanol and 1 mL of RO water, to prepare a 40 mg/mL benzylglycine ethyl ester solution.

1-2) A 0.5% acetylhyaluronic acid solution was prepared in the same manner as in Example 1.

1-3) A 40 mg/mL paclitaxel solution was prepared in the same manner as in Example 1.

1-4) A coating solution 4 was prepared by mixing 80 μL of the 40 mg/mL benzylglycine ethyl ester solution, 20 μL of the 0.5% acetylhyaluronic acid solution, and 100 μL of the 40 mg/mL paclitaxel solution.

(2) Coating of Balloon with Drug

A drug-eluting balloon was fabricated in the same manner as in Example 1, while using the coating solution 4 prepared above in such a manner that the amount of paclitaxel would be about 2 μg/mm$^2$.

Example 5

(1) Preparation of Coating Solution 5

1-1) L-Arginine ethyl ester dihydrochloride (CAS No. 36589-29-4) in an amount of 60 mg was weighed, and was added to and dissolved in an anhydrous ethanol-water mixed solution containing 1 mL of anhydrous ethanol and 1 mL of RO water, to prepare a 30 mg/mL arginine ethyl ester solution.

1-2) A 0.5% acetylhyaluronic acid solution was prepared in the same manner as in Example 1.

1-3) A 40 mg/mL paclitaxel solution was prepared in the same manner as in Example 1.

1-4) A coating solution 5 was prepared by mixing 80 μL of the 30 mg/mL arginine ethyl ester solution, 20 μL of the 0.5% acetylhyaluronic acid solution, and 100 μL of the 40 mg/mL paclitaxel solution.

(2) Coating of Balloon with Drug

A drug-eluting balloon was fabricated in the same manner as in Example 1, while using the coating solution 5 prepared above in such a manner that the amount of paclitaxel would be about 2 μg/mm$^2$.

Example 6

(1) Preparation of Coating Solution 6

1-1) N-α-Benzoyl-L-arginine ethyl ester hydrochloride (CAS No. 2645-08-1) in an amount of 60 mg was weighed, and was added to and dissolved in an anhydrous ethanol-water mixed solution containing 1 mL of anhydrous ethanol and 1 mL of RO water, to prepare a 30 mg/mL benzoyl-arginine ethyl ester solution.

1-2) A 0.5% acetylhyaluronic acid solution was prepared in the same manner as in Example 1.

1-3) A 40 mg/mL paclitaxel solution was prepared in the same manner as in Example 1.

1-4) A coating solution 6 was prepared by mixing 80 μL of the 30 mg/mL benzoyl-arginine ethyl ester solution, 20 μL of the 0.5% acetylhyaluronic acid solution, and 100 μL of the 40 mg/mL paclitaxel solution.

(2) Coating of Balloon with Drug

A drug-eluting balloon was fabricated in the same manner as in Example 1, while using the coating solution 6 prepared above in such a manner that the amount of paclitaxel would be about 2 μg/mm$^2$.

Example 7

(1) Preparation of Coating Solution 7

1-1) L-Dimethyl aspartate hydrochloride (CAS No. 32213-95-9) in an amount of 60 mg was weighed, and was added to and dissolved in an anhydrous ethanol-water mixed solution containing 1 mL of anhydrous ethanol and 1 mL of RO water, to prepare a 30 mg/mL dimethyl aspartate solution.

1-2) A 0.5% acetylhyaluronic acid solution was prepared in the same manner as in Example 1.

1-3) A 40 mg/mL paclitaxel solution was prepared in the same manner as in Example 1.

1-4) A coating solution 7 was prepared by mixing 80 μL of the 30 mg/mL dimethyl aspartate solution, 20 μL of the 0.5% acetylhyaluronic acid solution, and 100 μL of the 40 mg/mL paclitaxel solution.

(2) Coating of Balloon with Drug

A drug-eluting balloon was fabricated in the same manner as in Example 1, while using the coating solution 7 prepared above in such a manner that the amount of paclitaxel would be about 2 μg/mm$^2$.

Example 8

(1) Preparation of Coating Solution 8

1-1) L-Serine ethyl ester hydrochloride (CAS No. 26348-61-8) in an amount of 60 mg was weighed, and was added to and dissolved in an anhydrous methanol-water mixed solution containing 1 mL of anhydrous methanol and 1 mL of RO water, to prepare a 30 mg/mL serine ethyl ester solution.

1-2) A 0.5% acetylhyaluronic acid solution was prepared in the same manner as in Example 1.

1-3) A 40 mg/mL paclitaxel solution was prepared in the same manner as in Example 1.

1-4) A coating solution 8 was prepared by mixing 80 μL of the 30 mg/mL serine ethyl ester solution, 20 μL of the 0.5% acetylhyaluronic acid solution, and 100 μL of the 40 mg/mL paclitaxel solution.

(2) Coating of Balloon with Drug

A drug-eluting balloon was fabricated in the same manner as in Example 1, while using the coating solution 8 prepared above in such a manner that the amount of paclitaxel would be about 2 μg/mm$^2$.

Example 9

(1) Preparation of Coating Solution 9

1-1) Glycerine (CAS No. 56-81-5) in an amount of 100 μL was mixed with 100 μL of anhydrous ethanol, to prepare a 50% glycerine solution.

1-2) A 0.5% acetylhyaluronic acid solution was prepared in the same manner as in Example 1.

1-3) A 30 mg/mL valine methyl ester solution was prepared in the same manner as in Example 1.

1-4) A 40 mg/mL paclitaxel solution was prepared in the same manner as in Example 1.

1-5) A coating solution 9 was prepared by mixing 20 μL of the 50% glycerine solution, 40 μL of the 0.5% acetylhyaluronic acid solution, 80 μL of the 30 mg/mL valine methyl ester solution, and 100 μL of the 40 mg/mL paclitaxel solution.

(2) Coating of Balloon with Drug

A drug-eluting balloon was fabricated in the same manner as in Example 1, while using the coating solution 9 prepared above in such a manner that the amount of paclitaxel would be about 2 μg/mm$^2$.

Example 10

(1) Preparation of Coating Solution 10

1-1) A 50% glycerine solution was prepared in the same manner as in Example 9.

1-2) Sodium acetylhyaluronate (average molecular weight=100,000; degree of substitution with acetyl group=2.6 to 3.8/unit; CAS No. 287390-12-9) in an amount of 40 mg was weighed, and was added to and dissolved in an anhydrous ethanol-water mixed solution containing 0.8 mL of anhydrous ethanol and 3.2 mL of RO water, to prepare a 1% acetylhyaluronic acid solution.

1-3) L-Valine methyl ester hydrochloride (CAS No. 6306-52-1) in an amount of 210 mg was weighed, and was added to and dissolved in an anhydrous ethanol-water mixed solution containing 1.5 mL of anhydrous ethanol and 1.5 mL of RO water, to prepare a 70 mg/mL valine methyl ester solution.

1-4) Paclitaxel (CAS No. 33069-62-4) in an amount of 168 mg was weighed, and was added to and dissolved in 3 mL of tetrahydrofuran, to prepare a 56 mg/mL paclitaxel solution.

1-5) A coating solution 10 was prepared by mixing 168 μL of the 50% glycerine solution, 300 μL of the 1% acetylhyaluronic acid solution, 720 μL of the 70 mg/mL valine methyl ester solution, and 2,400 μL of the 56 mg/mL paclitaxel solution.

(2) Coating of Balloon with Drug

A drug-eluting balloon was fabricated in the same manner as in Example 1, while using the coating solution 10 prepared above in such a manner that the amount of paclitaxel would be about 3 μg/mm$^2$.

Example 11

(1) Preparation of Coating Solution 11

1-1) Sodium hyaluronate (average molecular weight=1,000,000; CAS No. 9067-32-7) in an amount of 5 mg was weighed, and was added to and dissolved in 1 mL of RO water, to prepare a 0.5% aqueous hyaluronic acid solution.

1-2) A 30 mg/mL valine methyl ester solution was prepared in the same manner as in Example 1.

1-3) A 40 mg/mL paclitaxel solution was prepared in the same manner as in Example 1.

1-4) A coating solution 11 was prepared by mixing 20 μL of the 0.5% aqueous hyaluronic acid solution, 80 μL of the 30 mg/mL valine methyl ester solution, and 100 μL of the 40 mg/mL paclitaxel solution.

(2) Coating of Balloon with Drug

A drug-eluting balloon was fabricated in the same manner as in Example 1, while using the coating solution 11 prepared above in such a manner that the amount of paclitaxel would be about 2 μg/mm$^2$.

Example 12

(1) Preparation of Coating Solution 12

1-1) Sodium butyryl hyaluronate (average molecular weight=100,000; degree of substitution with butyryl group=0.9/unit) in an amount of 5 mg was weighed, and was added to and dissolved in an anhydrous ethanol-water mixture containing 0.8 mL of anhydrous ethanol and 0.2 mL of RO water, to prepare a 0.5% butyryl hyaluronic acid solution.

1-2) A 30 mg/mL valine methyl ester solution was prepared in the same manner as in Example 1.

1-3) A 40 mg/mL paclitaxel solution was prepared in the same manner as in Example 1.

1-4) A coating solution 12 was prepared by mixing 30 μL of the 0.5% butyryl hyaluronic acid solution, 120 μL of the 30 mg/mL valine methyl ester solution, and 150 μL of the 40 mg/mL paclitaxel solution.

It is to be noted that the butyryl hyaluronic acid was synthesized by the method described in Japanese Patent No. 4323148, as described below.

Sodium hyaluronate (FCH-120, produced by Kikkoman Biochemifa Company) in an amount of 0.72 g was dissolved in 75 mL of pure water, and 1.0 g of distearyldimethylammonium chloride was suspended in 200 mL of pure water. Both of the resulting liquids were mixed with each other while stirring after warming to 45° C., and then the stirring was continued for five minutes. A complex thus produced was recovered by filtration, and was dried under a reduced pressure, to obtain a complex of hyaluronic acid and distearyldimethylammonium chloride. Next, 0.68 g of the thus obtained complex of hyaluronic acid and distearyldimethylammonium chloride was dissolved in N,N-dimethylformamide, to which 0.30 g of n-butyryl chloride and 0.25 g of pyridine were added, and the resultant mixture was stirred at 60° C. for two hours. After the reaction was over, 90 mL of a saturated ethanol solution of sodium acetate was added to the reaction mixture. A crystal precipitated was recovered by filtration, and was dried under a reduced pressure, to obtain butyryl hyaluronic acid.

(2) Coating of Balloon with Drug

A drug-eluting balloon was fabricated in the same manner as in Example 1, while using the coating solution 12 prepared above in such a manner that the amount of paclitaxel would be about 2 μg/mm$^2$.

Example 13

(1) Preparation of Coating Solution 13

1-1) Acetylhyaluronic acid (average molecular weight=5,000; degree of substitution with acetyl group=0.3/unit) in an amount of 5 mg was weighed, and was added to and dissolved in an anhydrous ethanol-water mixture containing 0.8 mL of anhydrous ethanol and 0.2 mL of RO water, to prepare a 0.5% acetylhyaluronic acid solution (Mw 5000).

1-2) A 30 mg/mL valine methyl ester solution was prepared in the same manner as in Example 1.

1-3) A 40 mg/mL paclitaxel solution was prepared in the same manner as in Example 1.

1-4) A coating solution 13 was prepared by mixing 20 μL of the 0.5% acetylhyaluronic acid solution (Mw 5000), 80 μL of the 30 mg/mL valine methyl ester solution, and 100 μL of the 40 mg/mL paclitaxel solution.

The acetylhyaluronic acid (average molecular weight=5,000; degree of substitution with acetyl group=0.3/unit) was synthesized by the method described in Japanese Patent No. 3142415, as described below.

Hyaluronic acid (Microhyaluronic acid FCH, produced by Kikkoman Biochemifa Company) in an amount of 1 g was added to 40 mL of acetic acid with stirring, followed by addition of 10 mL of anhydrous trifluoroacetic acid thereto, and the resulting mixture was stirred at room temperature for three hours. Next, 100 mL of pyridine and 50 mL of water were added to the mixture, then the reaction solution was slowly added to 100 mL of acetone, and a crystal produced was recovered by filtration, and was dried under a reduced pressure, to obtain acetylhyaluronic acid (average molecular weight=5,000; degree of substitution with acetyl group=0.3/unit).

(2) Coating of Balloon with Drug

A drug-eluting balloon was fabricated in the same manner as in Example 1, while using the coating solution 13 prepared above in such a manner that the amount of paclitaxel would be about 2 μg/mm$^2$.

Example 14

(1) Preparation of Coating Solution 14

Sodium acetylhyaluronate (average molecular weight=100,000; degree of substitution with acetyl group=2.6 to 3.8/unit; CAS No. 287390-12-9) in an amount of 10 mg was weighed, and was added to and dissolved in an anhydrous ethanol-water mixture containing 0.2 mL of anhydrous ethanol and 0.8 mL of RO water, to prepare a 1% acetylhyaluronic acid solution.

1-2) L-Phenylalanine ethyl ester hydrochloride (CAS No. 3182-93-2) in an amount of 90 mg was weighed, and was added to and dissolved in an anhydrous ethanol-water mixed solution containing 1.5 mL of anhydrous ethanol and 0.3 mL of RO water, to prepare a 50 mg/mL phenylalanine ethyl ester solution.

1-3) Paclitaxel (CAS No. 33069-62-4) in an amount of 80 mg was weighed, and was added to and dissolved in 2 mL of tetrahydrofuran, to prepare a 40 mg/mL paclitaxel solution.

1-4) A coating solution 14 was prepared by mixing 24 μL of the 1% acetylhyaluronic acid solution, 120 μL of the 50 mg/mL phenylalanine ethyl ester solution, and 360 μL of the 40 mg/mL paclitaxel solution.

(2) Coating of Balloon with Drug

A drug-eluting balloon was fabricated in the same manner as in Example 1, while using the coating solution 14 prepared above in such a manner that the amount of paclitaxel would be about 3 μg/mm$^2$.

Example 15

(1) Preparation of Coating Solution 15

1-1) A 1% acetylhyaluronic acid solution was prepared in the same manner as in Example 14.

1-2) L-Arginine ethyl ester dihydrochloride (CAS No. 36589-29-4) in an amount of 50 mg was weighed, and was added to and dissolved in an anhydrous ethanol-water mixed solution containing 0.5 mL of anhydrous ethanol and 0.5 mL of RO water, to prepare a 50 mg/mL arginine ethyl ester solution.

1-3) A 40 mg/mL paclitaxel solution was prepared in the same manner as in Example 14.

1-4) A coating solution 15 was prepared by mixing 24 μL of the 1% acetylhyaluronic acid solution, 120 μL of the 50 mg/mL arginine ethyl ester solution, and 360 μL of the 40 mg/mL paclitaxel solution.

(2) Coating of Balloon with Drug

A drug-eluting balloon was fabricated in the same manner as in Example 1, while using the coating solution 15 prepared above in such a manner that the amount of paclitaxel would be about 3 µg/mm².

Example 16

(1) Preparation of Coating Solution 16

1-1) A 1% acetylhyaluronic acid solution was prepared in the same manner as in Example 14.

1-2) L-Serine ethyl ester hydrochloride (CAS No. 26348-61-8) in an amount of 50 mg was weighed, and was added to and dissolved in an anhydrous ethanol-water mixed solution containing 0.5 mL of anhydrous ethanol and 0.5 mL of RO water, to prepare a 50 mg/mL serine ethyl ester solution.

1-3) A 40 mg/mL paclitaxel solution was prepared in the same manner as in Example 14.

1-4) A coating solution 16 was prepared by mixing 24 µL of the 1% acetylhyaluronic acid solution, 120 µL of the 50 mg/mL serine ethyl ester solution, and 360 µL of the 40 mg/mL paclitaxel solution.

(2) Coating of Balloon with Drug

A drug-eluting balloon was fabricated in the same manner as in Example 1, while using the coating solution 16 prepared above in such a manner that the amount of paclitaxel would be about 3 µg/mm².

Example 17

(1) Preparation of Coating Solution 17

1-1) A 1% acetylhyaluronic acid solution was prepared in the same manner as in Example 14.

1-2) Dimethyl L-aspartate hydrochloride (CAS No. 32213-95-9) in an amount of 50 mg was weighed, and was added to and dissolved in an anhydrous ethanol-water mixed solution containing 0.5 mL of anhydrous ethanol and 0.5 mL of RO water, to prepare a 50 mg/mL dimethyl aspartate solution.

1-3) A 40 mg/mL paclitaxel solution was prepared in the same manner as in Example 14.

1-4) A coating solution 17 was prepared by mixing 24 µL of the 1% acetylhyaluronic acid solution, 120 µL of the 50 mg/mL dimethyl aspartate solution, and 360 µL of the 40 mg/mL paclitaxel solution.

(2) Coating of Balloon with Drug

A drug-eluting balloon was fabricated in the same manner as in Example 1, while using the coating solution 17 prepared above in such a manner that the amount of paclitaxel would be about 3 µg/mm².

Example 18

(1) Preparation of Coating Solution 18

1-1) Sodium acetylhyaluronate (average molecular weight=100,000; degree of substitution with acetyl group=2.6 to 3.8/unit; CAS No. 287390-12-9) in an amount of 5 mg was weighed, and was added to and dissolved in an anhydrous ethanol-water mixture containing 0.2 mL of anhydrous ethanol and 0.8 mL of RO water, to prepare a 0.5% acetylhyaluronic acid solution.

1-2) L-Phenylalanine ethyl ester hydrochloride (CAS No. 3182-93-2) in an amount of 30 mg was weighed and was added to and dissolved in an anhydrous ethanol-water mixed solution containing 1.5 mL of anhydrous ethanol and 0.3 mL of RO water, to prepare a 30 mg/mL phenylalanine ethyl ester solution.

1-3) A 50% glycerine solution was prepared by mixing 500 µL of glycerine (CAS No. 56-81-5) with 500 µL of anhydrous ethanol.

1-4) Paclitaxel (CAS No. 33069-62-4) in an amount of 80 mg was weighed, then 1 mL of anhydrous ethanol and 1 mL of acetone were added thereto to effect dissolution, thereby preparing a 40 mg/mL paclitaxel solution.

1-5) A coating solution 18 was prepared by mixing 40 µL of the 0.5% acetylhyaluronic acid solution, 80 µL of the 30 mg/mL phenylalanine ethyl ester solution, 10 µL of the 50% glycerine solution, and 100 µL of the 40 mg/mL paclitaxel solution.

(2) Coating of Balloon with Drug

A drug-eluting balloon was fabricated in the same manner as in Example 1, while using the coating solution 18 prepared above in such a manner that the amount of paclitaxel would be about 3 µg/mm².

Example 19

(1) Preparation of Coating Solution 19

1-1) A 1% acetylhyaluronic acid solution was prepared in the same manner as in Example 14.

1-2) Dimethyl L-aspartate hydrochloride (CAS No. 32213-95-9) in an amount of 50 mg was weighed, and was added to and dissolved in an anhydrous ethanol-water mixed solution containing 0.5 mL of anhydrous ethanol and 0.5 mL of RO water, to prepare a 50 mg/mL dimethyl aspartate solution.

1-3) A 40 mg/mL paclitaxel solution was prepared in the same manner as in Example 14.

1-4) A coating solution 19 was prepared by mixing 24 µL of the 1% acetylhyaluronic acid solution, 120 µL of the 50 mg/mL dimethyl aspartate solution, and 360 µL of the 40 mg/mL paclitaxel solution.

(2) Coating of Balloon with Drug

A drug-eluting balloon was fabricated in the same manner as in Example 1, while using the coating solution 19 prepared above in such a manner that the amount of paclitaxel would be about 3 µg/mm².

Comparative Example C1

(1) Preparation of Coating Solution 21

1-1) L-Valine methyl ester hydrochloride (CAS No. 6306-52-1) in an amount of 54 mg was weighed, and was added to and dissolved in an anhydrous ethanol-water mixed solution containing 1.5 mL of anhydrous ethanol and 0.3 mL of RO water, to prepare a 30 mg/mL valine methyl ester solution.

1-2) Paclitaxel (CAS No. 33069-62-4) in an amount of 80 mg was weighed, and was added to and dissolved in an anhydrous ethanol-acetone mixed solution containing 1 mL of anhydrous ethanol and 1 mL of acetone, to prepare a 40 mg/mL paclitaxel solution.

1-3) A coating solution 21 was prepared by mixing 70 µL of the 30 mg/mL valine methyl ester solution and 50 µL of the 40 mg/mL paclitaxel solution.

(2) Coating of Balloon with Drug

A drug-eluting balloon was fabricated in the same manner as in Example 1, while using the coating solution 21 prepared above in such a manner that the amount of paclitaxel would be about 2 µg/mm².

Comparative Example C2

(1) Preparation of Coating Solution 22

1-1) L-Alanine ethyl ester hydrochloride (CAS No. 1115-59-9) in an amount of 80 mg was weighed, and was added to and dissolved in an anhydrous ethanol-water mixed solution containing 1 mL of anhydrous ethanol and 1 mL of RO water, to prepare a 40 mg/mL of an alanine ethyl ester solution.

1-2) A 40 mg/mL paclitaxel solution was prepared in the same manner as in Comparative Example C1.

1-3) A coating solution 22 was prepared by mixing 60 μL of the 40 mg/mL alanine ethyl ester solution and 50 μL of the 40 mg/mL paclitaxel solution.

(2) Coating of Balloon with Drug

A drug-eluting balloon was fabricated in the same manner as in Example 1, while using the coating solution 22 prepared above in such a manner that the amount of paclitaxel would be about 2 μg/mm$^2$.

Comparative Example C3

(1) Preparation of Coating Solution 23

1-1) L-Arginine hydrochloride (CAS No. 1119-34-2) in an amount of 60 mg was weighed, and was added to and dissolved in an anhydrous ethanol-water mixed solution containing 1 mL of anhydrous ethanol and 1 mL of RO water, to prepare a 30 mg/mL arginine solution.

1-2) A 40 mg/mL paclitaxel solution was prepared in the same manner as in Comparative Example C1.

(15.2) A coating solution 23 was prepared by mixing 60 μL of the 30 mg/mL arginine solution and 50 μL of the 40 mg/mL paclitaxel solution.

(2) Coating of Balloon with Drug

A drug-eluting balloon was fabricated in the same manner as in Example 1, while using the coating solution 23 prepared above in such a manner that the amount of paclitaxel would be about 2 μg/mm$^2$.

Comparative Example C4

(1) Preparation of Coating Solution 24

1-1) A 40 mg/mL paclitaxel solution was prepared in the same manner as in Comparative Example C1.

1-2) With 100 μL of the 40 mg/mL paclitaxel solution thus prepared, 100 μL of anhydrous ethanol was mixed, to prepare a 20 mg/mL paclitaxel solution, which was made to be a coating solution 24.

(2) Coating of Balloon with Drug

A drug-eluting balloon was fabricated in the same manner as in Example 1, while using the coating solution 24 prepared above in such a manner that the amount of paclitaxel would be about 3 μg/mm$^2$.

Comparative Example C5

(1) Preparation of Coating Solution 25

1-1) Hydrogenated soy phosphatidylcholine (SPC-3, produced by Lipoid GmbH; molecular weight: 790) in an amount of 100 mg was weighed, and was added to and dissolved in 2 mL of anhydrous ethanol, to prepare a 50 mg/mL hydrogenated soy phosphatidylcholine solution.

1-2) Sodium acetylhyaluronate (average molecular weight=100,000; degree of substitution with acetyl group=2.6 to 3.8/unit; CAS No. 287390-12-9) in an amount of 5 mg was weighed, and was added to and dissolved in an anhydrous ethanol-water mixture containing 0.8 mL of anhydrous ethanol and 0.2 mL of RO water, to prepare a 0.5% acetylhyaluronic acid solution.

1-3) A 40 mg/mL paclitaxel solution was prepared in the same manner as in Comparative Example C1.

1-4) A coating solution 25 was prepared by mixing 40 μL of the 50 mg/mL hydrogenated soy phosphatidylcholine solution, 120 μL of anhydrous ethanol, 40 μL of the 0.5% acetylhyaluronic acid solution, and 200 μL of the 40 mg/mL paclitaxel solution.

(2) Coating of Balloon with Drug

A drug-eluting balloon was fabricated in the same manner as in Example 1, while using the coating solution 25 prepared above in such a manner that the amount of paclitaxel would be about 3 μg/mm$^2$.

Comparative Example C6

(1) Preparation of Coating Solution 26

1-1) Phenylalanine-modified carboxymethyl cellulose (produced by ACROS; MW 90000; CAS No. 9004-32-4) in an amount of 10 mg was weighed, and was added to and dissolved in an anhydrous ethanol-water mixed solution containing 3.2 mL of anhydrous ethanol and 1.6 mL of RO water, to prepare a 0.1% solution of carboxymethyl cellulose-phenylalanine (carboxymethyl cellulose modified with phenylalanine methyl ester).

1-2) Sodium acetylhyaluronate (average molecular weight=100,000; degree of substitution with acetyl group=2.6 to 3.8/unit; CAS No. 287390-12-9) in an amount of 2 mg was weighed, and was added to and dissolved in an anhydrous ethanol-water mixture containing 0.8 mL of anhydrous ethanol and 0.2 mL of RO water, to prepare a 0.2% acetylhyaluronic acid solution.

1-3) A 40 mg/mL paclitaxel solution was prepared in the same manner as in Comparative Example C1.

1-4) A coating solution 26 was prepared by mixing 80 μL of the 0.1% carboxymethyl cellulose-phenylalanine solution, 40 μL of the 0.2% acetylhyaluronic acid solution, and 200 μL of the 40 mg/mL paclitaxel solution.

(2) Coating of Balloon with Drug

A drug-eluting balloon was fabricated in the same manner as in Example 1, while using the coating solution 26 prepared above in such a manner that the amount of paclitaxel would be about 3 μg/mm$^2$.

Comparative Example C7

A commercialized balloon catheter IN.PACT (produced by Invatec) was prepared.

Comparative Example C8

A balloon catheter (produced by Terumo Corporation, the material of a balloon (expandable portion) is nylon elastomer), whose expandable portion is sized to be 3.0 mm in diameter and 20 mm in length when expanded, was prepared. The balloon catheter in Comparative Example C8 is a non-drug-coated balloon that is not coated with a drug.
[Fabrication of Drug-Eluting Stent]

Example 20

(1) Preparation of Coating Solution 20
A coating solution 20 was prepared in the same manner as the coating solution 4 in Example 4.
(2) Coating of Stent with Drug
A stent (produced by Terumo Corporation) 2.5 mm by 18 mm in size was prepared.
The stent thus prepared was coated with the coating solution 20 so that the amount of paclitaxel would be about 1.5 µg/mm$^2$, by use of a pipette, followed by drying, to fabricate a drug-eluting stent.
[Measurement of the Amount of Paclitaxel in the Coating on the Balloon or Stent]
For the drug-eluting balloons in Examples 1 to 19 and Comparative Examples C1 to C6 and the drug-eluting stent in Example 20, the amount of paclitaxel in the coating on the balloon was measured.
1. Method
The drug-eluting balloon or drug-eluting stent fabricated above was immersed in a methanol solution, followed by shaking by use of a shaking machine for 10 minutes, whereby paclitaxel in the coating on the balloon was extracted. The absorptivity, at 227 nm, of the methanol solution into which paclitaxel had been extracted was measured by high performance liquid chromatography using an ultraviolet-visible absorptiometer, and the amount of paclitaxel per balloon ([µg/balloon]) or the amount of paclitaxel per stent ([µg/stent]) was determined. Furthermore, from the thus determined amount of paclitaxel and the balloon surface area or stent surface area, the amount of paclitaxel per unit area of the balloon or stent ([µg/mm$^2$]) was calculated.
2. Results (1) Examples 1 to 19 and Comparative Examples C1 to C6

Drug-Eluting Balloons

The results as set forth in Table 1 were obtained. In Table 1, 1 to 19 in the column of "Examples/Comparative examples" are Examples, and C1 to C6 in the column are Comparative Examples. Besides, in Table 1, "per each" under "Amount of PTX on a balloon" represents the amount of paclitaxel per each balloon (unit: µg/balloon), and "per unit area" under "Amount of PTX on a balloon" represents the amount of paclitaxel per 1 mm$^2$ of surface area of the balloon (unit: µg/mm$^2$), respectively.

TABLE 1

| Examples/ Comparative examples | Coating solution No. | Amount of PTX on a balloon | |
|---|---|---|---|
| | | per each [µ g/balloon] | per unit area [µ g/mm$^2$] |
| 1 | 1 | 549.6 | 2.9 |
| 2 | 2 | 391.1 | 2.1 |
| 3 | 3 | 382.7 | 2.0 |
| 4 | 4 | 382.1 | 2.0 |
| 5 | 5 | 284.9 | 1.5 |
| 6 | 6 | 272.0 | 1.4 |
| 7 | 7 | 308.3 | 1.6 |
| 8 | 8 | 270.5 | 1.4 |
| 9 | 9 | 305.1 | 1.6 |

TABLE 1-continued

| Examples/ Comparative examples | Coating solution No. | Amount of PTX on a balloon | |
|---|---|---|---|
| | | per each [µ g/balloon] | per unit area [µ g/mm$^2$] |
| 10 | 10 | 602.1 | 3.2 |
| 11 | 11 | 355.6 | 1.9 |
| 12 | 12 | 340.2 | 1.8 |
| 13 | 13 | 380.2 | 2.0 |
| 14 | 14 | 660.1 | 3.5 |
| 15 | 15 | 659.4 | 3.5 |
| 16 | 16 | 661.9 | 3.5 |
| 17 | 17 | 587.5 | 3.1 |
| 18 | 18 | 342.0 | 1.8 |
| 19 | 19 | 620.7 | 3.3 |
| C1 | 21 | 367.0 | 1.9 |
| C2 | 22 | 321.7 | 1.7 |
| C3 | 23 | 342.5 | 1.8 |
| C4 | 24 | 492.4 | 2.6 |
| C5 | 25 | 487.0 | 2.6 |
| C6 | 26 | 599.0 | 3.2 |

In Examples 1 to 19 and Comparative Examples C1 to C6, the amount of paclitaxel in the coating on the balloon was about 2 µg/mm$^2$ (Examples 2 to 9, 11 to 13 and 18, and Comparative Examples C1 to C3) or about 3 µg/mm$^2$ (Examples 1, 10, 14 to 17 and 19, and Comparative Examples C4 to C6), which means that an intended amount of paclitaxel could be provided in the coating on the balloon surface.

(2) Example 20

Drug-Eluting Stent

The results as set forth in Table 2 were obtained. In Table 2, 20 in the column of "Example" is Example. Besides, in Table 2, "per each" under "Amount of PTX on a stent" represents the amount of paclitaxel per each stent (unit: µg/stent), and "per unit area" under "Amount of PTX on a stent" represents the amount of paclitaxel per 1 mm$^2$ of surface area of the stent (unit: µg/mm$^2$), respectively.

TABLE 2

| Example | Coating solution No. | Amount of PTX on a stent | |
|---|---|---|---|
| | | per each [µ g/stent] | per unit area [µ g/mm$^2$] |
| 20 | 20 | 210.0 | 1.5 |

In Example 20, the amount of paclitaxel in the coating on the stent was 1.5 µg/mm$^2$, which means that an intended amount of paclitaxel could be provided in the coating on the stent surface.
Evaluation of Drug Coating Layer Durability by Use of Imitative Blood Vessel
In order to evaluate how much the drug coating layer is separated from the balloon in the process of delivery of the balloon to an affected part of a lesion, for the drug-eluting balloons in Examples 1 to 9 and 11 to 13 and Comparative Examples C1 to C4, a drug coating layer durability test using an imitative blood vessel was carried out by the following procedure.
1. Method
(1) A hollow imitative blood vessel 1 with a 90-degree angle was prepared, and a guiding catheter 2 (outside diameter: 5 Fr.) was inserted and passed in the imitative blood vessel 1 (see FIG. 1).

(2) The inside of the guiding catheter 2 was filled with PBS warmed up to 37° C.

(3) The drug-eluting balloon fabricated was folded by use of a wrapping machine.

(4) The balloon catheter 3 after the wrapping was inserted into the guiding catheter filled with the PBS, and a delivery operation of delivering the balloon 4 toward an outlet of the guiding catheter was performed for one minute.

(5) The balloon having been delivered in the guiding catheter was recovered, and the amount of paclitaxel remaining on the balloon (amount of PTX remaining) was determined by liquid chromatography. Furthermore, from the amount of paclitaxel in the coating on the drug-eluting balloon (amount of PTX coated on a balloon) and the amount of PTX remaining, the remaining rate of paclitaxel on the balloon (rates of PTX remaining) was calculated.

2. Results

The results as set forth in Table 3 were obtained. In Table 3, 1 to 9 and 11 to 13 in the column of "Examples/Comparative examples" are Examples, and C1 to C4 in the column are Comparative Examples. Besides, in Table 3, "Amount of PTX coated on a balloon" represents the amount of paclitaxel provided in the coating per each drug-eluting balloon (unit: μg/balloon), "Amount of PTX remaining on a balloon" represents the amount of paclitaxel remaining per each balloon after the delivery operation (unit: μg/balloon), and "Rates of PTX remaining on a balloon" represents the rates of paclitaxel remaining on the balloon after the delivery operation (unit: mass %).

Figure 2:
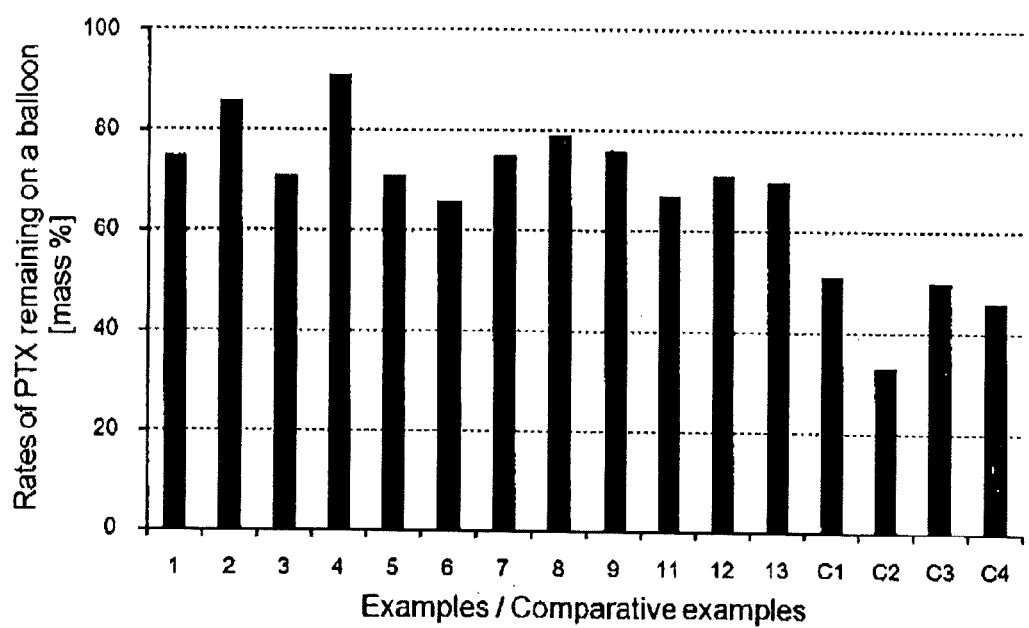
FIG. 2 is a graph representing the rate of paclitaxel remaining on the balloon after a delivery operation of drug-eluting balloons in Examples 1 to 9, 11 to 13 and Comparative Examples C1 to C4, in evaluation of durability of a drug coating layer using the imitative blood vessel.

In addition, FIG. 2 shows a graph representing rates of paclitaxel remaining on the balloon after the delivery operation of the drug-eluting balloon in Examples 1 to 9 and 11 to 13 and Comparative Examples C1 to C4, in the drug coating layer durability evaluation using the imitative blood vessel. In FIG. 2, the axis of abscissas represents Examples or Comparative Examples, wherein numerals 1 to 9 and 11 to 13 mean Examples 1 to 9 and 11 to 13, respectively, and alphabet-accompanied numerals C1 to C4 mean Comparative Examples C1 to C4, respectively. The axis of ordinates represents the remaining rate of paclitaxel on the balloon after the delivery operation (unit: mass %). The "mass %" means "% by mass."

TABLE 3

| Examples/Comparative examples | Amount of PTX coated on a balloon [μ g/balloon] | Amount of PTX remaining on a balloon [μ g/balloon] | Rates of PTX remaining on a balloon [mass %] |
|---|---|---|---|
| 1 | 549.6 | 412.1 | 75 |
| 2 | 391.1 | 336.3 | 86 |
| 3 | 382.7 | 271.7 | 71 |
| 4 | 382.1 | 347.7 | 91 |
| 5 | 284.9 | 202.3 | 71 |
| 6 | 272.0 | 179.5 | 66 |
| 7 | 308.3 | 231.2 | 75 |
| 8 | 270.5 | 213.7 | 79 |
| 9 | 305.1 | 231.9 | 76 |
| 11 | 355.6 | 238.3 | 67 |
| 12 | 340.2 | 241.5 | 71 |
| 13 | 380.2 | 266.1 | 70 |
| C1 | 367.0 | 187.2 | 51 |
| C2 | 321.7 | 106.1 | 33 |
| C3 | 342.5 | 171.3 | 50 |
| C4 | 492.4 | 226.5 | 46 |

In this evaluation system, in the case where the amount of the drug remaining on the balloon after the delivery operation is equal to or more than 60 mass %, the ability to hold the drug during the delivery operation is good, and a substantial amount of drug can be delivered to the affected part of a lesion. When the amount is below 60 mass %, on the other hand, a substantial amount of the drug is peeled during the delivery operation, which is undesirable from the viewpoint of safety. In this case, the amount of drug that can be delivered to the affected part of a lesion is small, and, therefore, satisfactory transfer of the drug to the tissue cannot be expected. Accordingly, in this evaluation system, when the amount of paclitaxel remaining on the balloon after the delivery operation is equal to or more than 60 mass %, it can be judged that a good ability to hold the drug during the delivery process is secured.

For the drug-eluting balloons fabricated in Examples 1 to 9 and 11 to 13, the amounts of paclitaxel remaining on the balloon after the delivery operation were equal to or more than 60 mass % based on the amount in the coating. On the other hand, for the drug-eluting balloons fabricated in Comparative Examples C1 to C4, the amounts of paclitaxel remaining on the balloon were in the range of 33 to 51 mass %, every one of which was below 60 mass %.

From the results above, it has been verified that the drug coating layer containing the hyaluronic acid derivative and the amino-acid ester according to described aspects enhances adhesion of paclitaxel to the balloon, and enhances the ability to hold the drug during the delivery operation.

Evaluation of Transferability of Drug to Tissue in Rabbit Iliac Artery

For the drug-eluting balloons in Examples 1, 7, 9, 12 and 14 to 18 and Comparative Examples C5 to C7, transferability of paclitaxel to blood vessel tissue after one hour from expansion of the balloon in a rabbit iliac artery was evaluated by the following procedure.

1. Method (1) A guide wire was inserted into a right iliac artery or a left iliac artery of a rabbit under radioscopic observation. Next, the drug-eluting balloon (having an expandable portion sized to be 3.0 mm in diameter and 20 mm in length when expanded) was transferred along the guide wire to the iliac artery.

(2) The balloon was expanded at 7 atm for one minute. Immediately thereafter, the balloon was pulled out.

(3) After 60 minutes from the expansion of the balloon, a blood vessel (a range of about 3.5 cm from branching) was sampled.

(4) Methanol was added to the sampled blood vessel, followed by homogenization, to obtain a tissue homogenate.

(5) The tissue homogenate was analyzed by high performance liquid chromatography, to determine the amount of paclitaxel contained in the tissue (the amount of paclitaxel per 1 g of tissue). Furthermore, from the amount of paclitaxel in the coating on the drug-eluting balloon and the amount of paclitaxel remaining on the balloon, the remaining rate of paclitaxel on the balloon (rate of PTX remaining on a balloon) was calculated.

2. Results

The results as set forth in Table 4 were obtained. In Table 4, numerals 1, 7, 9, 12 and 14 to 18 in the column of "Examples/Comparative examples" are Examples, and C5 to C7 in the column are Comparative Examples. In Table 4, "Amount of PTX contained in tissue" represents the amount of paclitaxel contained in 1 g of blood vessel tissue (unit: μg/g tissue), "Rates of PTX transferred to tissue" represents the rates of paclitaxel transferred from the coating on the balloon into the blood vessel tissue (unit: mass %), and "Rates of PTX remaining on a balloon" represents the rates of paclitaxel remaining on the balloon (unit: mass %), respectively.

Figure 3:
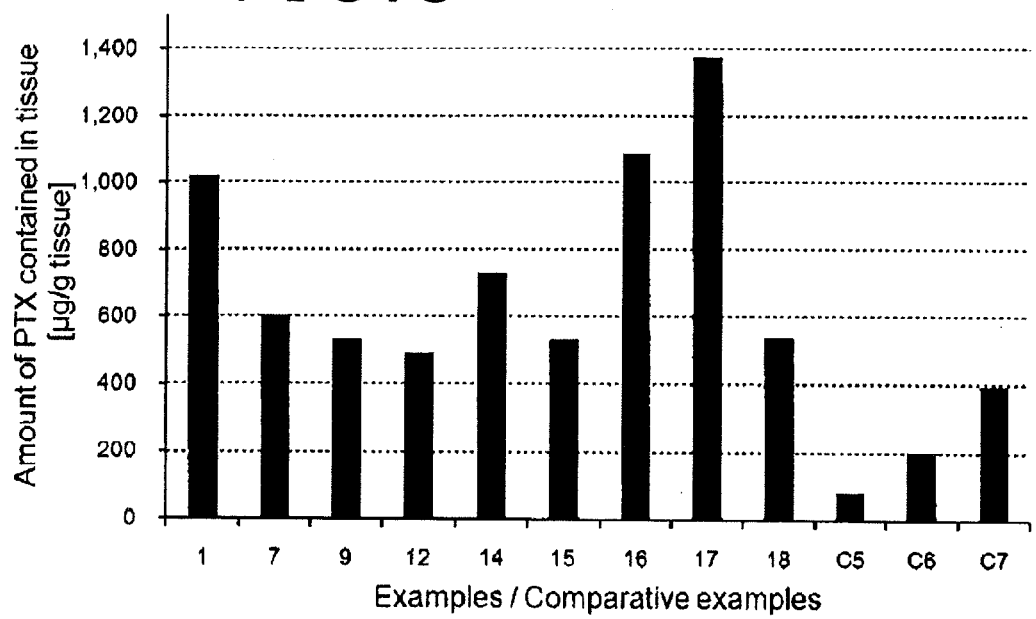
FIG. 3 is a graph representing the amount of paclitaxel contained in a blood vessel tissue in Examples 1, 7, 9, 12 and 14 to 18 and Comparative Examples C5 to C7, in evaluation of transferability of a drug to a tissue in a rabbit iliac artery.

In addition, FIG. 3 shows a graph representing the amount of paclitaxel contained in the blood vessel tissue in Examples 1, 7, 9, 12 and 14 to 18 and Comparative Examples C5 to C7, in the evaluation of transferability of the drug to the tissue in a rabbit iliac artery. In FIG. 3, the axis of abscissas represents Examples or Comparative Examples, wherein numerals 1, 7, 9, 12 and 14 to 18 mean Examples 1, 7, 9, 12 and 14 to 18, respectively, and alphabet-accompanied numerals C5 to C7 mean Comparative Examples C5 to C7, respectively. The axis of ordinates represents the amount of paclitaxel contained in 1 g of blood vessel tissue (unit: μg/g tissue). The "μg/g tissue" means micrograms per gram of tissue.

TABLE 4

| Examples/ Comparative examples | Amount of PTX contained in tissue [μ g/g tissue] | Rates of PTX transferred to tissue [mass %] | Rates of PTX remaining on a balloon [mass %] |
|---|---|---|---|
| 1 | 1018.5 | 8.9 | 4.3 |
| 7 | 602.6 | 4.2 | 6.1 |
| 9 | 532.5 | 4.8 | 7.3 |
| 12 | 491.4 | 2.1 | 3.7 |
| 14 | 727.8 | 2.8 | 7.2 |
| 15 | 532.6 | 2.3 | 12.2 |
| 16 | 1087.5 | 4.5 | 22.1 |
| 17 | 1377.8 | 6.2 | 15.1 |
| 18 | 538.4 | 4.6 | 12.1 |
| C5 | 80.4 | 0.2 | 11.8 |
| C6 | 201.1 | 1.0 | 2.2 |
| C7 | 398.2 | 1.7 | 20.4 |

For every one of Examples 1, 7, 9 and 14 to 18, the amount of PTX contained in the tissue recovered after 60 minutes from the expansion in the blood vessel was more than 500 μg per 1 g of tissue. On the other hand, for every one of Comparative Examples C5 to C7, the amount was below 400 μg per 1 g of tissue. For Example 12, the amount was below 500 μg per 1 g of tissue, but the amount was proximate to 500 μg, meaning that the amount of PTX contained in the tissue in Example 12 was clearly above those in Comparative Examples C5 to C7.

From the results above, it has been verified that paclitaxel present in the coating together with the hyaluronic acid derivative and the amino-acid ester shows sufficient transferability of the drug to the tissue. In addition, it has also been clarified that the drug-eluting balloons according to the described aspects are very high in the transferability of drug to tissue, as compared with IN.PACT, which is a commercialized drug-eluting balloon. Furthermore, it has been found that the paclitaxel coat layer in which glycerine is mixed into a combination of a hyaluronic acid derivative and an amino-acid ester is also high in the transferability of drug to tissue.

Evaluation of Retention of Drug in Tissue in Rabbit Abdominal Aorta

For the drug-eluting balloons in Example 19, the amount of paclitaxel contained in tissue after one hour and after 24 hours from expansion of the balloon in a rabbit abdominal aorta was determined, and the retention of drug was thereby evaluated, by the following procedure.

1. Method (1) The drug-eluting balloon was subjected to wrapping, followed by premounting of a stent thereon. The drug-eluting balloon with the stent premounted thereon was put to use.

(2) After a guide wire was inserted into an abdominal aorta of a rabbit under radioscopic observation, a guiding catheter was pulled out while holding the position of the guide wire. Next, the drug-eluting balloon (having an expandable portion sized to be 3.0 mm in diameter and 20 mm in length when expanded) with the stent premounted thereon was transferred along the guide wire to the abdominal aorta.

(3) The balloon was expanded at 7 atm for one minute. Immediately thereafter, the balloon was pulled out.

(4) After one hour and after 24 hours from the expansion of the balloon, a blood vessel (a range of about 3.5 cm from branching) was sampled.

(5) Methanol was added to the thus sampled blood vessel, followed by homogenization, to obtain a tissue homogenate.

(6) The tissue homogenate was analyzed by high performance liquid chromatography, to determine the amount of paclitaxel contained in the tissue (the amount of paclitaxel per 1 g of tissue) after one hour and after 24 hours from the expansion of the balloon. Furthermore, from the amount of paclitaxel present in the coating on the drug-eluting balloon and the amounts of paclitaxel contained in the tissue after one hour and after 24 hours from the expansion of the balloon, rates of transfer of paclitaxel to tissue (rates of PTX transferred to tissue) after one hour and after 24 hours from the expansion of the balloon were calculated, and the remaining rate (rate of PTX remaining on a balloon) was calculated from the amount of paclitaxel remaining on the balloon.

2. Results

The results as set forth in Table 5 were obtained. In Table 5, numeral 19 in the column of "Example" is Example. Besides, in Table 5, "Amount of PTX contained in tissue" represents the amount of paclitaxel contained in 1 g of blood vessel tissue (unit: μg/g tissue), "Rates of PTX transferred to tissue" represents the rates of paclitaxel transferred from the coating on the balloon into the blood vessel tissue (unit: mass %), and "Rates of PTX remaining on a balloon" represents the rates of paclitaxel remaining on the balloon (unit: mass %). Furthermore, "1H" and "24H" in the columns of "Amount of PTX contained in tissue" and "Rates of PTX transferred to tissue" mean one hour after the expansion of blood vessel lumen and 24 hours after the expansion of blood vessel lumen, respectively.

Figure 4:
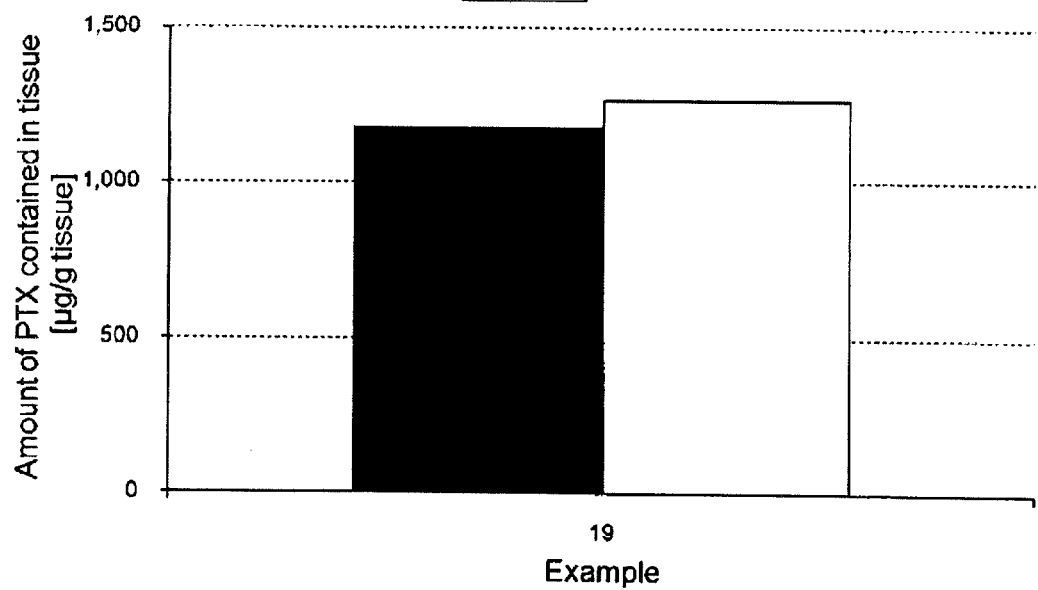
FIG. 4 is a graph representing the amount of paclitaxel remaining in a blood vessel tissue after one hour and after 24 hours from expansion of the blood vessel lumen in Example 19, in evaluation of retention of a drug in a tissue in a rabbit abdominal aorta.

FIG. 4 shows a graph representing the amount of paclitaxel remaining in the blood vessel tissue after one hour and after 24 hours from the expansion of the blood vessel lumen in Example 19, in evaluation of retention of drug in tissue in a rabbit abdominal aorta. In FIG. 4, the axis of abscissas represents Example, wherein numeral 19 means Example 19. The axis of ordinates represents the amount of paclitaxel contained in 1 g of blood vessel tissue (unit: μg/g tissue). In the legend, "1H" and "24H" mean one hour after the expansion of blood vessel lumen and 24 hours after the expansion of blood vessel lumen, respectively. The "μg/g tissue" means "micrograms per gram of tissue."

TABLE 5

| Example | Amount of PTX contained in tissue [μ g/g tissue] | | Rates of PTX transferred to tissue [mass %] | | Rates of PTX remaining on a balloon [mass %] |
|---|---|---|---|---|---|
| | 1 H | 24 H | 1 H | 24 H | |
| 19 | 1176.8 | 1268.0 | 2.7 | 6.3 | 14.9 |

The amounts of paclitaxel contained in the tissue after one hour and after 24 hours from the expansion in the blood vessel lumen had approximately equal values, suggesting that the amount of paclitaxel in the tissue does not attenuate largely with the lapse of time. From this, it has been verified that a drug coating layer containing a hyaluronic acid derivative, an amino-acid ester and paclitaxel ensures that a sufficient amount of the drug is retained in the tissue for a long period of time, after the transfer of the drug to the tissue.

Evaluation of Effectiveness in Swine Coronary Artery

For the drug-eluting balloons in Example 10 as well as Comparative Example C7 and Comparative Example C8, the effectiveness in a swine coronary artery was evaluated by the following procedure.

1. Method (1) A guiding catheter was inserted via an 8 Fr. sheath, together with a guide wire, and was guided to left and right coronary artery orifices of a swine under radioscopic observation.

(2) Angiography was applied to each coronary artery (coronary artery: left anterior descending coronary artery (LAD), right coronary artery (RCA), left circumflex coronary artery (LCX)), and the blood vessel diameter of the coronary artery obtained by the angiography was measured by a QCA software.

(3) A part where the diameter of the stent is 1.2 times the blood vessel diameter and the diameter of the drug-eluting balloon is 1.3 times the blood vessel diameter was selected, and operations from a stent placement operation were carried out there.

(4) The stent (stent sized to be 3 mm in diameter and 15 mm in length) was expanded to 1.2 times in size in the selected coronary artery for 30 seconds, and then a balloon catheter for placing the stent indwelling was pulled out. In the stent indwelling site, the drug-eluting balloon (balloon sized to be 3 mm in diameter and 20 mm in length) was expanded to a diameter of 1.3 times the blood vessel diameter for one minute, and then the catheter was pulled out.

(5) After the expansion of the drug-eluting balloon was over, the guiding catheter and the sheath were pulled out, and the central side of the carotid artery was ligated. Thereafter, at an external opening of wound of a cervical part, the dissected muscles were sutured with a surgical suture, and skins were sutured with a skin-suturing stapler.

(4) After 28 days from the expansion of the balloon, autopsy was conducted. At the time of the autopsy, coronary angiography was conducted, whereby the patency (stenosis rate) in the stent indwelling site was checked, and the blood vessel diameter was measured. The stenosis rate (%) was calculated from the average blood vessel diameter immediately after balloon expansion and the average blood vessel diameter after 28 days.

2. Results

The results as set forth in Table 6 were obtained. In Table 6, numeral 10 in the column of "Examples/Comparative examples" is Example, and C7 and C8 in the column are Comparative Examples.

FIG. 5 shows a graph representing blood vessel stenosis rate in Example 10 and Comparative Examples C7 and C8, in evaluation of effectiveness in a swine coronary artery. In FIG. 5, the axis of abscissas represents Example or Comparative Examples, wherein numeral 10 means Example 10, whereas alphabet-accompanied numerals C7 and C8 mean Comparative Examples C7 and C8, respectively. The axis of ordinates represents blood vessel stenosis rate (unit: %).

TABLE 6

| Examples/Comparative examples | Stenosis rates [%] | S.D. |
| --- | --- | --- |
| 10 | 11.5 | 9.98 |
| C7 | 17.1 | 5.48 |
| C8 | 35.0 | 14.28 |

In Comparative Example C8, which is an example of treatment with a non-drug-coated balloon prepared as a non-drug-coated control, the stenosis rate of a blood vessel was 35.0%.

The stenosis rate of a blood vessel treated with IN.PACT prepared in Comparative Example C7 was 17.1%.

On the other hand, the stenosis rate of a blood vessel treated with the drug-eluting balloon fabricated in Example 10 was 11.5%.

From the results above, it has been verified that a drug coating layer containing acetylhyaluronic acid, an amino-acid ester, glycerine and paclitaxel shows a good stenosis-restraining or suppressing effect.

When a medical device (for example, balloon catheter) coated with the coating composition according to the described aspects is used, a drug can be efficiently delivered to the affected part of a lesion while restraining or suppressing separation of the drug coating layer from the medical device during the process of delivery to the affected part of the lesion. In addition, rapid release of the drug from the medical device at the affected part of the lesion can be promoted, and transferability of the drug to the tissue can be enhanced.

The detailed description above describes a coating composition for a drug-eluting medical device, a drug coating layer of a drug-eluting medical device and/or a drug-eluting medical device coated with the coating composition. The invention is not limited, however, to the precise embodiments and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A coating composition for a drug-eluting medical device, the coating composition containing:

a water-insoluble drug;

at least one compound selected from the group consisting of hyaluronic acid, alkanoyl hyaluronic acids obtained by substituting at least part of hydrogen atoms in hydroxyl groups of hyaluronic acid with an alkanoyl group, and salts of hyaluronic acid and the alkanoyl hyaluronic acids; and at least one compound selected from the group constituting of amino-acid esters and salts thereof, wherein the amino-acid is selected from the group consisting of alanine, cysteine, valine, leucine, isoleucine, methionine and phenylalanine.

2. The coating composition according to claim 1, wherein the alkanoyl group is represented by the following formula:

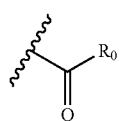

where $R_0$ is selected from the group consisting of alkyl groups of up to five carbon atoms, benzyl group and phenyl group.

3. The coating composition according to claim 1, wherein the alkanoyl group is at least one selected from the group consisting of acetyl group, propionyl group, isobutyryl group and butyryl group.

4. The coating composition according to claim 1, wherein the number of the hydrogen atoms in the hydroxyl groups that are substituted with the alkanoyl group is, on an average, 0.01 to 4 per unit of the hyaluronic acid.

5. The coating composition according to claim 1, wherein the average molecular weight of the at least one selected from the group consisting of hyaluronic acid, alkanoyl hyaluronic acids obtained by substituting at least part of the hydrogen atoms in the hydroxyl groups of the hyaluronic acid with an alkanoyl group, and salts of hyaluronic acid and the alkanoyl hyaluronic acids is $5 \times 10^3$ to $2 \times 10^5$.

6. The coating composition according to claim 1, wherein the amino-acid ester is a methyl ester or ethyl ester of any one amino acid selected from the group consisting of L-alanine, L-cysteine, L-isoleucine, L-leucine, L-methionine, L-phenylalanine, and L-valine.

7. The coating composition according to claim 1, wherein the mass ratio (A/B) of the content (A) of hyaluronic acid, the alkanoyl hyaluronic acid obtained by substituting at least part of the hydrogen atoms in the hydroxyl groups of hyaluronic acid with an alkanoyl group or the salt of hyaluronic acid or the alkanoyl hyaluronic acid to the content (B) of the amino-acid ester or the salt thereof is in the range from 0.0008 to 0.8 (mass/mass).

8. The coating composition according to claim 1, further containing a lower alcohol.

9. The coating composition according to claim 8, wherein the lower alcohol is glycerine.

10. The coating composition according to claim 1, wherein the water-insoluble drug is at least one selected from the group consisting of rapamycin, paclitaxel, docetaxel and everolimus.

11. A medical device comprising a drug coating layer formed on at least part of a surface of the medical device by use of the coating composition according to claim 1.

12. A medical device which is radially expandable within a lumen and which is coated with the coating composition according to claim 1.

13. The medical device according to claim 12, wherein the medical device that is radially expandable within the lumen is a balloon catheter or a stent.

14. A method Of treatment, comprising:
a step of delivering the medical device according to claim 12 into a lumen;
a step of radially expanding the medical device within the lumen; and
a step of eluting a drug from a drug coating layer formed on at least part of a surface of the medical device and allowing the drug to act on the lumen.

15. A method of treatment, comprising:
a step of delivering the medical device according to claim 13 into a lumen;
a step of radially expanding the medical device within the lumen; and
a step of eluting a drug from a drug coating layer formed on at least part of a surface of the medical device and allowing the drug to act on the lumen.

* * * * *